US009339790B2

(12) United States Patent
Vittadello et al.

(10) Patent No.: US 9,339,790 B2
(45) Date of Patent: May 17, 2016

(54) CHEMICALLY MODIFIED GRAPHENE

(75) Inventors: Michele Vittadello, Lawrenceville, NJ (US); Kamil Woronowicz, Morris Plains, NJ (US); Manish Chhowalla, Highland Park, NJ (US); Paul G. Falkowski, Princeton, NJ (US); John W. Harrold, Jr., Pittstown, NJ (US)

(73) Assignees: RESEARCH FOUNDATION OF THE CITY UNIVERSITY OF NEW YORK, New York, NY (US); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 175 days.

(21) Appl. No.: 14/118,596

(22) PCT Filed: May 18, 2012

(86) PCT No.: PCT/US2012/038626
§ 371 (c)(1),
(2), (4) Date: Feb. 4, 2014

(87) PCT Pub. No.: WO2012/159051
PCT Pub. Date: Nov. 22, 2012

(65) Prior Publication Data
US 2014/0154770 A1     Jun. 5, 2014

Related U.S. Application Data

(60) Provisional application No. 61/601,862, filed on Feb. 22, 2012, provisional application No. 61/601,691, filed on Feb. 22, 2012, provisional application No. 61/546,740, filed on Oct. 13, 2011, provisional application No. 61/488,011, filed on May 19, 2011.

(51) Int. Cl.
*B01J 20/289* (2006.01)
*C07K 1/22* (2006.01)
(Continued)

(52) U.S. Cl.
CPC ............ *B01J 20/289* (2013.01); *B01J 20/3206* (2013.01); *B01J 20/3219* (2013.01);
(Continued)

(58) Field of Classification Search
CPC .. B01J 20/289; B01J 20/3206; B01J 20/3219; B01J 20/3265; C07K 1/22; C07K 2319/20; C07K 2319/21; C12N 11/02; C12N 11/14; G01N 30/02; G01N 30/48; G01N 30/482; G01N 33/20; G01N 33/68; G01N 33/6803; G01N 33/6854; G01N 1/18; Y10T 436/17; Y10T 436/173845; Y10T 436/18; Y10T 436/20; Y10T 436/200833; Y10T 436/203332; Y10T 436/23; Y10T 436/25; Y10T 436/25125; Y10T 436/25375; Y10T 436/255
USPC .......... 436/72, 73, 79, 80, 81, 83, 84, 85, 86, 436/106, 111, 119, 127, 128, 131, 145, 161, 436/174, 175, 177, 178; 422/69, 70, 72, 422/527, 533; 423/414, 415.1, 460; 530/350, 387.1; 556/138; 549/212
See application file for complete search history.

(56) References Cited

U.S. PATENT DOCUMENTS

2007/0092432 A1   4/2007   Prud'Homme et al.
2010/0081057 A1   4/2010   Liu et al.

FOREIGN PATENT DOCUMENTS

CN         101773855 A       7/2010
WO      WO2008097343 A2      8/2008
(Continued)

OTHER PUBLICATIONS

Supplementary Partial European Search Report, EP 12786582, Feb. 20, 2015.
(Continued)

*Primary Examiner* — Maureen Wallenhorst
(74) *Attorney, Agent, or Firm* — Hoffmann & Baron, LLP

(57) ABSTRACT

This disclosure relates to graphene derivatives, as well as related devices including graphene derivatives and methods of using graphene derivatives.

24 Claims, 9 Drawing Sheets

(51) Int. Cl.
| | |
|---|---|
| G01N 33/68 | (2006.01) |
| G01N 30/02 | (2006.01) |
| C25B 9/16 | (2006.01) |
| C25B 1/00 | (2006.01) |
| B01J 20/32 | (2006.01) |
| C12N 11/02 | (2006.01) |
| C12N 11/14 | (2006.01) |
| C12P 3/00 | (2006.01) |
| C12P 7/06 | (2006.01) |
| B01J 20/281 | (2006.01) |

(52) U.S. Cl.
CPC .............. B01J20/3265 (2013.01); C07K 1/22 (2013.01); C12N 11/02 (2013.01); C12N 11/14 (2013.01); C12P 3/00 (2013.01); C12P 7/06 (2013.01); C25B 1/003 (2013.01); C25B 9/16 (2013.01); *C07K 2319/20* (2013.01); *C07K 2319/21* (2013.01); *G01N 30/482* (2013.01); *Y02E 50/17* (2013.01)

(56) References Cited

FOREIGN PATENT DOCUMENTS

| | | | |
|---|---|---|---|
| WO | WO2009143405 | A2 | 11/2009 |
| WO | WO2010014215 | A2 | 2/2010 |
| WO | WO2010074918 | A1 | 7/2010 |
| WO | 2011/082064 | * | 7/2011 |

OTHER PUBLICATIONS

Trojer et al., "Characterisation and Evaluation of Metal-Loaded Iminodiacetic Acid-Silica of Different Porosity for the Selective Enrichment of Phosphopeptides", Journal of Chromatography A., vol. 1079 (2005), pp. 197-207.

Hainfeld et al., "Ni-NTA-Gold Clusters Target His-Tagged Proteins", Journal of Structural Biology, vol. 127 (1999), pp. 185-198.

Xu et al., "A Graphene Hybrid Material Covalently Functionalized with Porphyrin: Synthesis and Optical Limiting Property", Advanced Materials, vol. 21 (2009), pp. 1275-1279.

Ren et al., "DNA Cleavage System of Nanosized Graphene Oxide Sheets and Copper Ions", ACS Nano, vol. 4, No. 12, (2010), pp. 7169-7174.

Kou et al., "Making Silica Nanoparticle-Covered Graphene Oxide Nanohybrids as General Building Blocks for Large-Area Superhydrophilic Coatings", Nanoscale, vol. 3 (2011), pp. 519-528.

Geng et al., "Porphyrin Functionalized Graphene Sheets in Aqueous Suspensions: From the Preparation of Graphene Sheets to Highly Conductive Graphene Films", Journal of Physical Chemistry C., vol. 114 (2010), pp. 8227-8234.

Lightcap et al., "Anchoring Semiconductor and Metal Nanoparticles on a Two-Dimensional Catalyst Mat. Storing and Shuttling Electrons with Reduced Graphene Oxide", Nano Letters, vol. 10 (2010), pp. 577-583.

Muszynski et al., "Decorating Graphene Sheets with Gold Nanoparticles", Journal of Physical Chemistry C., vol. 112 (2008), pp. 5263-5266.

Kodali et al., "Nonperturbative Chemical Modification of Graphene for Protein Micropatterning", Langmuir Letter, vol. 27, No. 3 (2011), pp. 863-865.

Li et al., "Nitrilotriacetic Acid-Coated Magnetic Nanoparticles as Affinity Probes for Enrichment of Histidine-Tagged Proteins and Phosphorylated Peptides", Analytical Chemistry, vol. 79, No. 19 (2007), pp. 7519-7525.

* cited by examiner

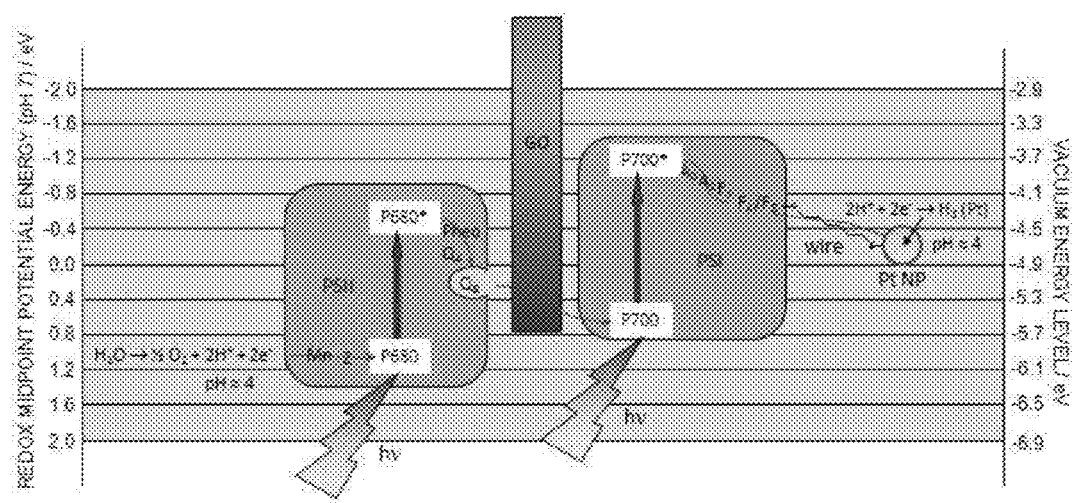
Fig. 5 Conceptual schematic of a viable PSII/PSI/Pt-NP/GO photoelectrochemical system on a redox energy scale. The corresponding vacuum energy level is also indicated.

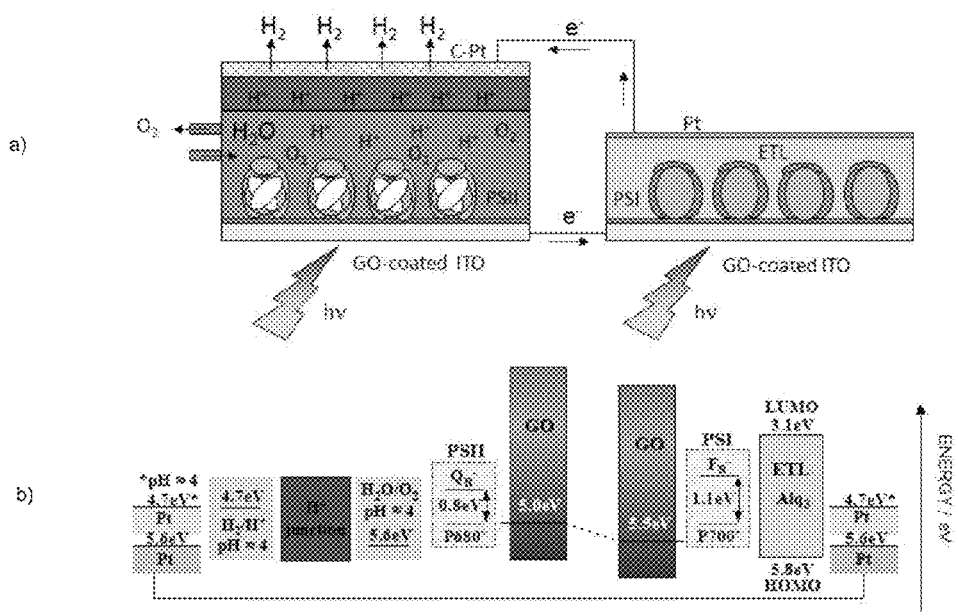

Fig. 6 a) Schematic of a solid state integrated PSII/PSI/GO galvanic system for water photolysis; b) corresponding energy level diagram indicating the vacuum work function energies of the metals and GO, the redox level of the relevant semi-reactions, the energy gaps of PSII, PSI and HOMO/LUMO energies of $Alq_3$. Beside the vacuum work function of Pt, its expected energy level (*) in solution at pH=4 is indicated. A direct transfer from PSII to GO is considered.

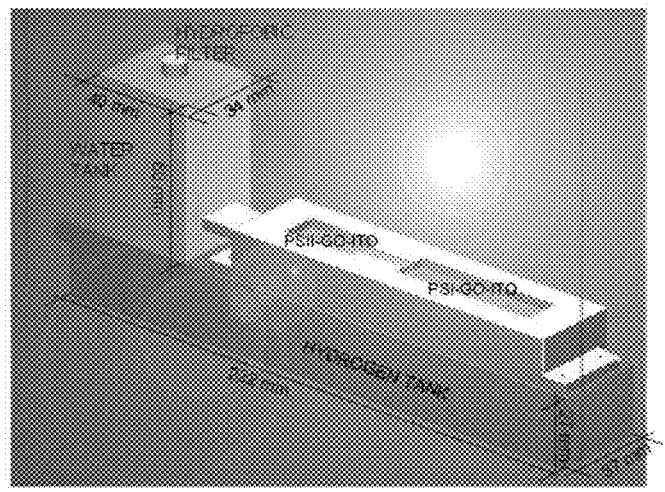
Fig. 7 a) CAD design of a PSII/PSI/GO photoelectrochemical cell for hydrogen generation/compression
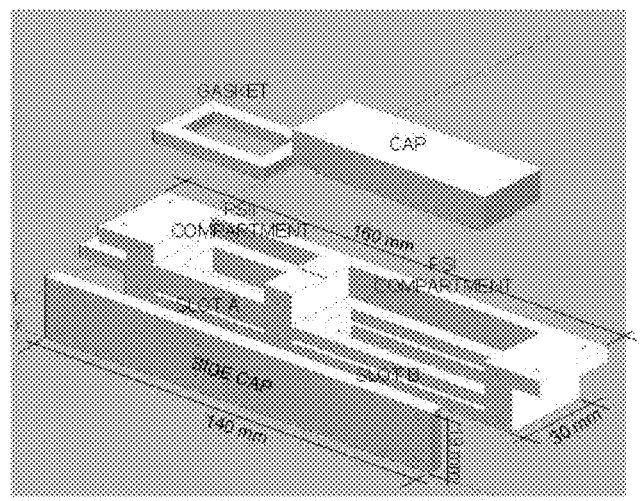
Fig. 7 b) details of the Teflon core.

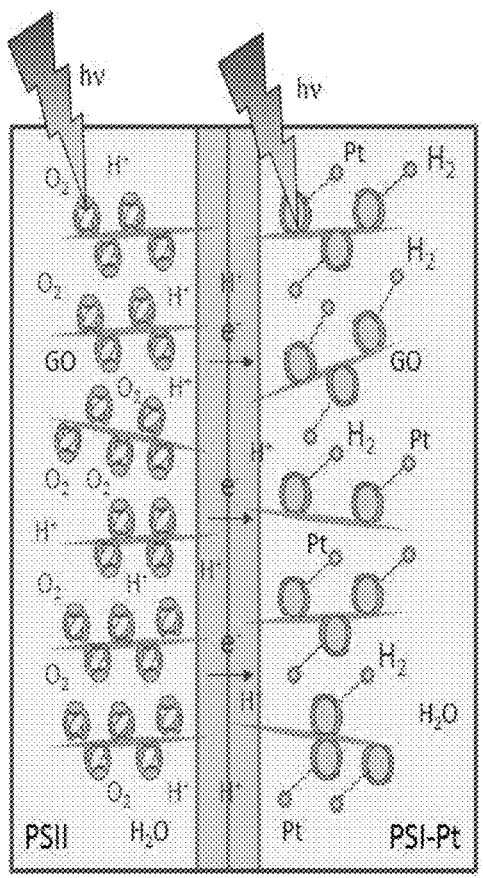
Fig. 8 a) Schematic of a PSII/PSI/GO-Polymer galvanic system for water photolysis.

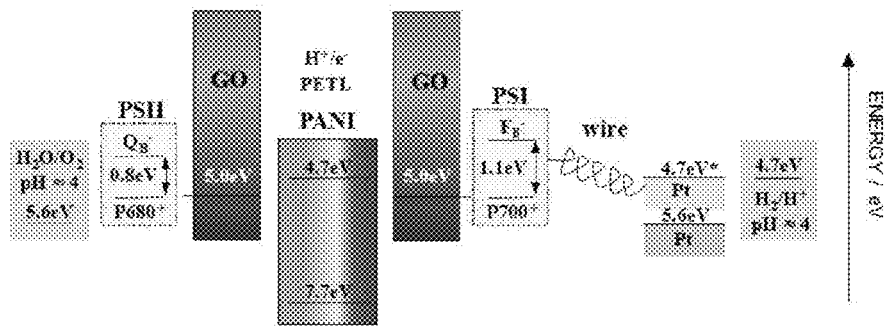

Fig. 8 b) corresponding energy-level diagram to schematic 8 a) indicating the vacuum work function energies of the metals and GO, the redox level of the relevant semi-reactions, and the energy gaps of PSII and PSI. Beside the vacuum work function of Pt, its expected energy level (*) in solution at pH=4 is indicated. A direct transfer from PSII and PSI to GO is considered.

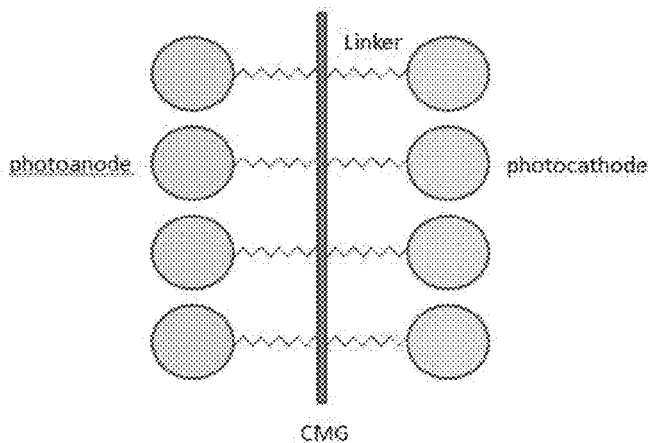

Fig. 9 Schematic of a single CMG platelet bearing self-assembled photoanode and photocathode nanoparticles. The resulting system is capable of hydrogen or other fuel generation depending on the specific identity of the nanoparticles and their surface modifications.

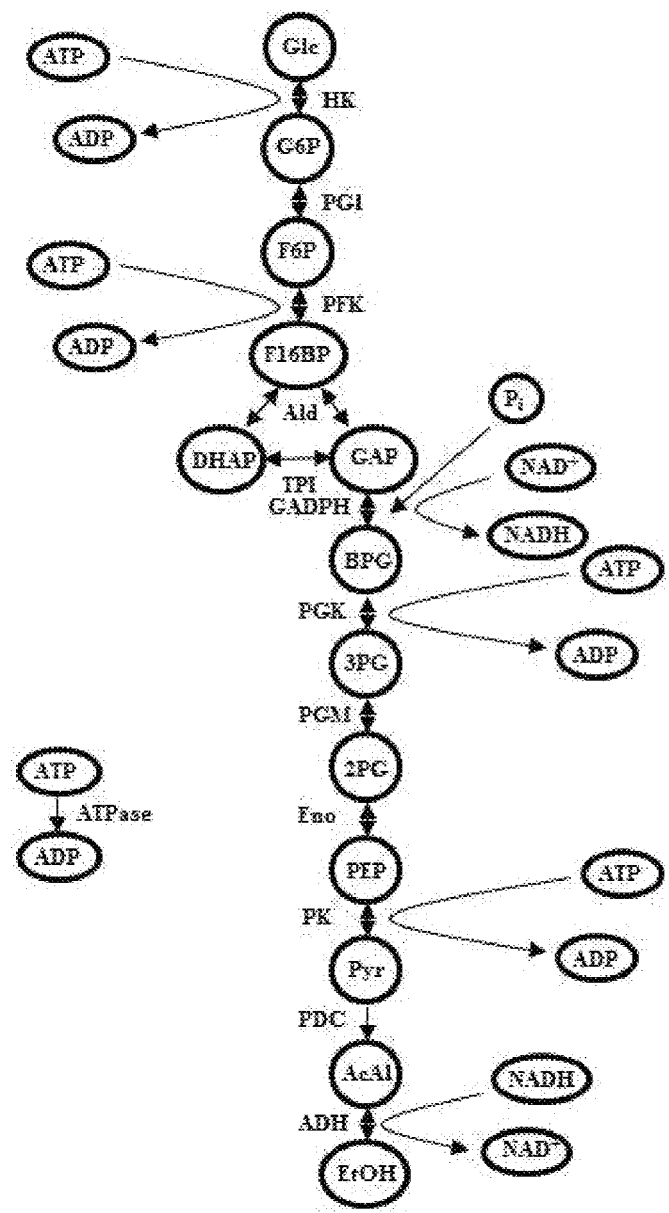
Fig. 10 Glycolytic ethanol production pathway. Metabolites are circled and enzyme abbreviations are noted adjacent to the reaction catalyzed.

CHEMICALLY MODIFIED GRAPHENE

CROSS-REFERENCE TO RELATED APPLICATIONS

This application claims priority to International Application No. PCT/US2012/038626 filed May 18, 2012, which claims priority to U.S. Provisional Application Ser. No. 61/488,011, filed May 19, 2011; U.S. Provisional Application Ser. No. 61/546,740, filed Oct. 13, 2011; U.S. Provisional Application Ser. No. 61/601,691, filed Feb. 22, 2012; and U.S. Provisional Application Ser. No. 61/601,862, filed Feb. 22, 2012. The entire contents of which are hereby incorporated by reference.

STATEMENT REGARDING FEDERALLY SPONSORED RESEARCH

This invention was supported by contract number FA9550-10-1-0091 awarded by Air Force Office of Scientific Research and grant number CBET-1260073 awarded by the National Science Foundation Early-concept Grants for Exploratory Research. The U.S. Government has certain rights in the invention.

TECHNICAL FIELD

This disclosure relates to graphene derivatives, as well as related devices and methods.

BACKGROUND

Proteins (e.g., enzymes and antibodies) are often difficult to isolate while still maintaining their biological activity. For example, such biomolecules may require use of solvents other than water for their isolation, which can denature the biomolecules and complicate the isolation process. However, it is important that proteins that are used as drugs are highly pure for patients' health and for regulatory compliance. It is also important to develop more efficient high throughput purification methods to reduce costs and environmental impact.

Graphene is a monolayer of carbon atoms having a two-dimensional honeycomb structure containing six-member carbon rings, and is a basic building block for graphitic materials of all other dimensionalities. For example, the crystalline flake form of graphite consists of many graphene sheets stacked together. Thus, graphene sometimes is referred to as monolayer graphite. The sheet structure of graphene provides this material with unique electronic and optical properties.

SUMMARY

This disclosure is based on an unexpected discovery that chromatographic stationary phase materials made from certain graphene derivatives exhibit superior performance in protein isolation compared to conventional stationary phase materials.

In one aspect, this disclosure features a material (e.g., a resin material for a stationary phase) that includes a graphene derivative containing a graphene core and a first pendant group. The first pendant group includes a metal ion, a nanoparticle, a sulfonate group, an amine group, a quaternary ammonium group, or a chelating group.

In another aspect, this disclosure features a material that includes a graphene derivative containing a graphene core and a protein (as a pendant group) covalently bonded to the graphene core.

In another aspect, this disclosure features a chromatography column containing at least one of the above materials.

In another aspect, this disclosure features a chromatographic system that includes the above chromatography column.

In another aspect, this disclosure features a method of isolating a protein from a sample. The method includes (1) disposing the sample in a dispersion containing at least one of the above materials, thereby binding the protein to the material to form a protein-bound material, (2) isolating the protein-bound material, and (3) recovering the protein from the protein-bound material.

In still another aspect, this disclosure features a method of preparing graphene oxide. The method includes (1) reacting graphite sequentially with an oxidizing acid and an oxidant to form an oxidized graphene; (2) washing the oxidized graphene with an aqueous solvent; and (3) treating the oxidized graphene with a solution containing an intercalant to form graphene oxide.

Embodiments can include one or more of the following features.

In some embodiments, the first pendant group can include a metal ion (e.g., $Ni^{2+}$, $Cu^{2+}$, $Zn^{2+}$, $Ag^+$, $Fe^{3+}$, $Ga^{3+}$, $Zr^{3+}$, $Ca^{2+}$, or $Co^{2+}$). In such embodiments, the first pendant group can include a linking group and the metal ion is complexed with the linking group. The linking group can include a nitrilotriacetic acid moiety, a tris-nitrilotriacetic acid moiety, or an iminodiacetic acid moiety. In some embodiments, the linking group can be covalently bonded to the graphene core through an amide group (e.g., —CO—NH—). In some embodiments, the first pendant group can further include a His-tagged protein (e.g., His-tagged Protein A or His-tagged Protein G) binding to the metal ion.

In some embodiments, the first pendant group can include a nanoparticle. In some embodiments, the nanoparticle can be a $TiO_2$ or $SiO_2$ nanoparticle. For example, the $SiO_2$ nanoparticle can be covalently bonded to the graphene core through an amide group. In some embodiments, the $SiO_2$ nanoparticle can be covalently bonded to the graphene core through a linkage —CO—NH—R—Si(—O—)$_3$, in which R is $C_1$-$C_{20}$ alkylene.

In some embodiments, the graphene derivative can further include a second pendant group containing a metal ion or a $TiO_2$ nanoparticle.

In some embodiments, the first pendant group can include a protein (e.g., Protein A, Protein G, or an E72G3 protein). The protein can be covalently bonded to the graphene core. In such embodiments, the material can further include a linking group covalently bonded to the graphene core and the protein. The linking group can include an acetamide moiety, a succinimide moiety, a maleimide moiety, or a thiosulfate moiety.

In some embodiments, the first pendant group can include a sulfonate group, an amine group, a quaternary ammonium group, or a chelating group. For example, the first pendant group can include —(CO)$_x$—NH—R—SO$_3$H, —(CO)$_x$—NH—R—N(R'R''R''')$^+$, —(CO)$_x$—NH—R—N(R'R''), —(CO)$_x$—NH—R—SH, —(CO)$_x$—NH—R—COOH, —(CO)$_x$—NH—R—N(CH$_2$COOH)$_2$, —(CO)$_x$—NH—R—NH—R—PO$_3$H, or an EDTA derivative, wherein x is 0 or 1; each R, independently, is $C_1$-$C_{20}$ alkylene; and each of R', R'', and R''', independently, is H or $C_1$-$C_{20}$ alkyl.

In some embodiments, the material can be in the form of a powder, a liquid-based composition, or a film.

In some embodiments, the column can further include a spacer mixed with the material. For example, the spacer can be an oxide (e.g., a metal oxide) or a polymer.

In some embodiments, isolating the protein-bound material can be carried out by centrifugation, filtration, or decantation.

In some embodiments, the protein to be isolated can be a His-tagged protein (e.g., a His-tagged photosystem I core complex, a His-tagged photosystem II core complex, or a His-tagged bacterial reaction center), a FLAG-tagged protein, a HA-tagged protein, a myc-tagged protein, a GST-tagged protein, a MBP-tagged protein, a lectin, a phosphoprotein (e.g., an Fc receptor, a Ulk antibody, a calcineurin, a K chromatin immunoprecipitate, or a urocotin), or an antibody having an Fc region.

In some embodiments, the oxidizing acid is nitric acid

In some embodiments, the oxidant is potassium chlorate.

In some embodiments, the intercalant is tetrabutylammonium hydroxide.

In some embodiments, treating the oxidized graphene includes heating the oxidized graphene in the solution containing the intercalant at a temperature of at least about 60° C. (e.g., at least about 80° C.).

In another aspect, a device for producing hydrogen is claimed which includes a graphene derivative suspended in an aqueous solution, wherein the graphene derivative includes a graphene core, a first pendant group, and a second pendant group, wherein the first pendant group includes a first linking group attached to the graphene core and a photocathode nanoparticle; and the second pendant group includes a second linking group attached to the graphene core and a photoanode nanoparticle.

In some embodiments, each of the first and second linking group includes a nitrilotriacetic acid moiety.

In some embodiments, the first pendant group further includes a metal ion coordinated with the first linking group and the second pendant group further includes a second metal ion coordinated with the second linking group.

In some embodiments, each of the first and second metal ions is $Ni^{2+}$.

In some embodiments, the photocathode nanoparticle includes a first His-tagged protein binding to the first metal ion and the photoanode nanoparticle includes a second His-tagged protein binding to the second metal ion.

In some embodiments, the first His-tagged protein includes a His-tagged photosystem I core complex and the second His-tagged protein includes a His-tagged photosystem II core complex.

In some embodiments, the first pendant group further includes a platinum nanoparticle or a hydrogenase.

In some embodiments, the platinum nanoparticle is bonded to the His-tagged photosystem I core complex or the platinum nanoparticle is bonded to the His-tagged photosystem I core complex through $—S—(CH_2)_6—S—$.

In some embodiments, the photocathode includes a first semiconductor and the photoanode includes a second semiconductor.

In some embodiments, the first semiconductor is coated with a catalyst for a hydrogen evolving reaction and the second semiconductor is coated with a catalyst for an oxygen evolving reaction.

In another embodiment, a device for producing hydrogen is claimed including first and second transport layers; a first graphene layer including a first graphene derivative, the first transport layer between the first graphene layer and the second transport layer; and a second graphene layer including a second graphene derivative, the second transport layer between the first transport layer and the second graphene layer.

The first graphene derivative includes a first graphene core and a first pendant group, the first pendant group includes a first linking group covalently bonded to the first graphene core, a first metal ion coordinated with the first linking group, and a first His-tagged protein binding to the first metal ion.

The second graphene derivative includes a second graphene core and a second pendant group, the second pendant group includes a second linking group covalently bonded to the second graphene core, a second metal ion coordinated with the second linking group, and a second His-tagged protein binding to the second metal ion.

Each of the first and second linking group includes a nitrilotriacetic acid moiety. Each of the first and second metal ions is $Ni^{2+}$. The first His-tagged protein includes a His-tagged photosystem I core complex; and the second His-tagged protein includes a His-tagged photosystem II core complex.

In some embodiments, the first and second transport layers include a polyaniline or a sulfonated polyaniline.

In some embodiments, the first pendant group further comprises a platinum nanoparticle or a hydrogenase. The platinum nanoparticle may be bonded to the His-tagged photosystem I core complex or bonded to the His-tagged photosystem I core complex through $—S—(CH_2)_6—S—$.

In some embodiments, the device may further include first and second housings, wherein the first housing, together with the first transport layer, defines a first compartment and the second housing, together with the second transport layer, defines a second compartment.

In some embodiments, the first graphene layer is disposed in the first compartment and the second graphene layer is disposed in the second compartment.

Embodiments can have one or more of the following advantages.

Without wishing to be bound by theory, it is believed that the graphene derivative described herein (e.g., a graphene derivative containing a metal ion or a protein) can have a significantly higher protein loading capacity than a conventional stationary phase material.

Without wishing to be bound by theory, it is believed that the graphene derivative described herein (e.g., a graphene derivative containing a metal ion or a protein) can be used as a stationary phase in a chromatographic method to effectively isolate a protein from a sample while maintaining the biological activities of the protein. By contrast, although a conventional stationary phase material may be able to isolate a protein, it often deactivates the protein during the isolation process.

Other features, objects, and advantages will be apparent from the description, drawings, and claims.

DESCRIPTION OF DRAWINGS

FIG. 5 is a schematic of a viable PSII/PSI/Pt-NP/GO photoelectrochemical system on a redox energy scale. The corresponding vacuum energy level is also indicated.

FIG. 6 a) is a schematic of a solid state integrated PSII/PSI/GO galvanic system for water photolysis; b) corresponding energy level diagram indicating the vacuum work function energies of the metals and GO, the redox level of the relevant semi-reactions, the energy gaps of PSII, PSI and HOMO/LUMO energies of $Alq_3$.

FIG. 7 a) is a CAD design of a PSII/PSI/GO photoelectrochemical cell for hydrogen generation/compression; b) details of the Teflon core.

FIG. 8 a) is a Schematic of a PSII/PSI/GO-Polymer galvanic system for water photolysis; b) corresponding energy-level diagram to schematic 8 a) indicating the vacuum work function energies of the metals and GO, the redox level of the relevant semi-reactions, and the energy gaps of PSII and PSI.

FIG. 9 is a schematic of a single CMG platelet bearing self-assembled photoanode and photocathode nanoparticles.

FIG. 10 is a schematic of a glycolytic ethanol production pathway.

Like reference symbols in the various drawings indicate like elements.

DETAILED DESCRIPTION

In general, this disclosure relates to a graphene derivative containing a graphene core and at least one pendant group (e.g., at least two pendant groups, at least five pendant groups, or at least 10 pendant groups) on the graphene core. The pendant groups can include a metal ion, a nanoparticle, a protein, a sulfonate group, an amine group, a quaternary ammonium group, a chelating group, or a combination thereof. In some embodiments, a pendant group can include one or more linking groups covalently, ionically, or coordinatively bonded to the above mentioned groups (e.g., a metal ion or a protein). The linking group can be covalently bonded (e.g., through an amide group or an ester group) to the graphene core. In some embodiments, the graphene derivative can have one or more pendant groups different from the other pendant groups. In some embodiments, the graphene derivative can include a plurality of graphene cores covalently bonded (e.g., cross-linked) by one or more polymers.

Graphene Derivatives Containing a Metal Ion

Figure 1:
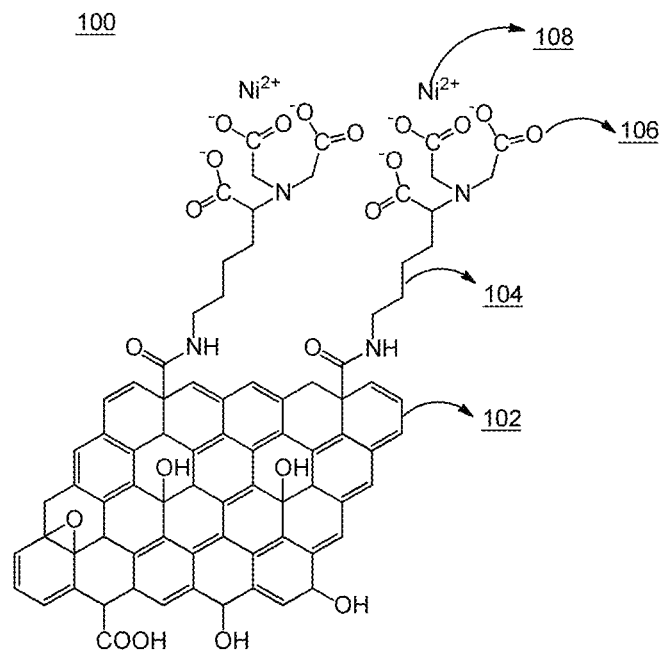
FIG. 1 is an embodiment of a graphene derivative containing a metal ion.

FIG. 1 illustrates an embodiment of a graphene derivative containing a metal ion. Specifically, referring to FIG. 1, a graphene derivative 100 includes a graphene core 102 and a pendant group 104. Pendant group 104 includes a linking group 106 and a metal ion 108 complexed (e.g., ionically or coordinatively) with the linking group.

In some embodiments, linking group 106 is covalently bonded (e.g., through an amide group or an ester group) to graphene core 102. In the embodiment shown in FIG. 1, linking group 106 includes a chelating group (i.e., a nitrilotriacetic acid moiety) at one end, an amide group at the other end, and a spacer group (i.e., a butylene group) between the chelating group and the amide group. In general, the chelating group can complex with metal ion 108 and therefore entrap metal ion 108 on the surface of the graphene derivative. Any suitable chelating group capable of complexing with a metal ion can be used in linking group 106. Exemplary chelating groups include a nitrilotriacetic acid moiety, a tris-nitrilotriacetic acid moiety, or an iminodiacetic acid moiety. In some embodiments, the spacer group in linking group 106 can be any suitable $C_1$-$C_{20}$ alkylene group. Without wishing to be bound by theory, it is believed that including a spacer group in linking group 106 can increase the protein loading capacity of graphene derivative 100.

Metal ion 108 can generally serve as affinity ligand to isolate or purify various proteins by forming a complex (e.g., through coordinative binding) with certain amino acid residues (e.g., His, Glu, Asp, Tyr, Cys, Arg, Lys, and Met residues) on the surface of the proteins. Exemplary metal ions include $Ni^{2+}$, $Cu^{2+}$, $Zn^{2+}$, $Ag^+$, $Fe^{3+}$, $Ga^{3+}$, $Zr^{3+}$, $Ca^{2+}$, and $Co^{2+}$.

In general, the amino acid residues capable of binding with the metal ion on a protein to be isolated can exist in the amino acid sequence of a naturally occurring protein or can be can be added to a naturally occurring protein as a tag. Exemplary of tagged proteins include His-tagged proteins, FLAG-tagged proteins, HA-tagged proteins, myc-tagged proteins, GST-tagged proteins, and MBP-tagged proteins. For example, a His tag containing 2-10 neighboring His residues (e.g., 2, 3, 4, 5, 6, 7, 8, 9, or 10 His residues) can be introduced to an end (e.g., N-terminal or C-terminal) or an accessible internal sequence of a protein to form a His-tagged protein. Exemplary His-tagged protein include His-tagged photosystem I core complex, a His-tagged photosystem II core complex, His-tagged bacterial reaction center, His-tagged Protein A, and His-tagged Protein G. Other examples of tagged proteins are described in, e.g., Gaberc-Porekar et al., *J. Biochem. Biophys. Methods*, 49 (2001) 335-360 and Ueda et al., *J. Chromatography A*, 988 (2003) 1-23. A protein containing amino acid residues capable of binding with a metal ion can have strong affinity with the graphene derivative described herein. As such, the graphene derivative described herein can selectively adsorb (e.g., through coordinative binding) such a protein and isolate it from other components (e.g., other proteins) in a sample.

In some embodiments, graphene derivative 100 can include a plurality of other functional groups bonded to graphene core 102. Exemplary functional groups include those typically found in a graphene oxide (e.g., carboxyl, hydroxyl, and epoxy) and those introduced into a graphene oxide by additional chemical modifications (e.g., amino).

Without wishing to be bound by theory, it is believed that the graphene derivative described herein (e.g., a graphene derivative containing a metal ion or a protein) can have a significantly higher protein loading capacity than a conventional stationary phase material (e.g., when used in affinity chromatography). For example, the graphene derivative can have a protein loading capacity of at least about 100 mg per milliliter (mg/mL) (e.g., at least about 200 mg/mL, at least about 400 mg/mL, at least about 500 mg/mL, at least about 1,000 mg/mL, at least about 2,000 mg/mL, at least about 4,000 mg/mL) and/or at most about 10,000 mg/mL (e.g., at most about 9,000 mg/mL, at most about 7,000 mg/mL, at most about 5,000 mg/mL, at most about 3,000 mg/mL, or at most about 1,000 mg/mL) of the graphene derivative measured by a Chlorophyll a assay. As another example, the graphene derivative can have a protein loading capacity of at least about 60 mg/mL (e.g., at least about 80 mg/mL, at least about 100 mg/mL, at least about 150 mg/mL, at least about 200 mg/mL, at least about 300 mg/mL, at least about 400 mg/mL) and/or at most about 500 mg/mL (e.g., at most about 350 mg/mL, at most about 250 mg/mL, at most about 150 mg/mL, at most about 110 mg/mL, or at most about 90 mg/mL) of the graphene derivative measured by an amino acid analysis. By contrast, the protein loading capacity of a conventional stationary phase material for affinity chromatography is at most about 60 mg/mL measured by a commercial protein assay kit.

In addition, without wishing to be bound by theory, it is believed that the graphene derivative described herein (e.g., a graphene derivative containing a metal ion or a protein) can have a high protein loading capacity for large proteins (e.g., having a molecular weight of at least about 61 kDa) or multiple protein complexes (e.g., photosystem I or II core complex), while still maintaining their biological activities during protein binding or isolation using the graphene derivative described herein. By contrast, to the inventors' knowledge, polysaccharide-based resins currently available on the market appear to have a relatively high protein loading capacity only for small proteins (e.g., having a molecular weight less than about 61 kDa). Further, to the inventors' knowledge, there are no proteins above 61 kDa reported to bind in high protein loading (e.g., greater than 10 mg/ml) with any resin available on the market for immobilized-metal affinity chromatography (IMAC). Without wishing to be bound by theory, it is believed that this is probably due to the limited pore size of the commercial polysaccharide-based IMAC resins, which significantly reduce the ability of larger proteins to access the metal coordination sites within the polysaccharide matrix. Moreover, it appears that commercially available polysaccharide-based IMAC resins can obtain a higher protein loading capacity for denatured proteins than proteins in native conditions due to higher accessibility of the His-tag in the denatured proteins. However, although refolding of denatured peptide chains may result in active proteins, this approach is typically limited to individual domains or proteins not requiring chaperones and other cofactors for folding, but will not be applicable to large proteins or multiple protein complexes (e.g., photosystem I or II core complex). Without wishing to be bound by theory, it is believed that the graphene derivative described herein can have a high protein loading capacity for large proteins (e.g., having a molecular weight of at least about 61 kDa) or complex quaternary proteins (e.g., photosystem I or II core complex) without denaturing these proteins, thereby maintaining their biological activities during an isolation process.

A graphene derivative can be prepared by using graphene oxide as a starting material. Graphene oxide can be prepared by methods known in the art or can be purchased from a commercial source. As an example, graphene oxide can be prepared by treating graphite with a strong oxidizer (e.g., a mixture of $H_2SO_4$, $NaNO_3$, and $KMnO_4$). The oxidation treatment typically forms oxygen-containing functional groups (e.g., COOH, OH, and epoxy groups) on exfoliated graphite, which results in graphene oxide. Graphene oxide can have an oxygen content of from about 8 mol % to about 35 mol %. The oxygen content can be adjusted by treating a graphene oxide with a strong reductant (e.g., hydrazine) at different concentrations and treatment periods. As a starting material, the graphene oxide can be in the form of a powder, a liquid-based composition (which can be formed by suspending or dispersing the powder in an aqueous solvent) such as a suspension or a slurry, or a film coated on a substrate. In general, the substrates can be made from any suitable materials, such as plastics, metals (e.g., gold), metal oxides, quartz, paper, or glass.

In some embodiments, the graphene oxide can be cross-linked by a polymer (e.g., a polyallylamine) to form a cross-linked graphene oxide. Such a cross-linked oxide can also be used as a starting material to form a graphene derivative described herein.

In some embodiments, a graphene derivative containing a metal ion can be prepared by (1) optionally activating the carboxyl groups on a graphene oxide (e.g., by using N-hydroxysuccinimide (NHS) and N-ethyl-N'-(3-dimethylaminopropyl)-carbodiimide (EDC)) suspended in an aqueous solvent or in a film on a substrate, (2) reacting the optionally activated graphene oxide with a compound having a chelating group (e.g., a nitrilotriacetic acid moiety) at one end and a group (e.g., an amino or hydroxyl group) capable of reacting with carboxyl or its activated form at the other end to form a modified graphene oxide, and (3) reacting the modified graphene oxide with a metal salt (e.g., $NiSO_4$) to form a graphene derivative containing a metal ion. When a graphene oxide in the form of a liquid-based composition is used as a starting material, each of the above reaction steps can be followed by a mild centrifugation and/or filtration to separate the product of each step from its reaction medium. By doing so, one can remove any excess reactant in the reaction medium from the product of each reaction step. When a graphene oxide in the form of a film is used as a starting material, the film can be washed by a solvent (e.g., water) after each of the above reaction steps to remove any excess reactant on the surface of the film.

In some embodiments, the graphene oxide used to prepare the graphene derivative described herein can be made environmentally stable. To prepare such a graphene oxide, one can first react graphite sequentially with an oxidizing acid (e.g., nitric acid) and an oxidant (e.g., potassium chlorate) to form an oxidized graphene; (2) washing the oxidized graphene with an aqueous solvent (e.g., water); and (3) treating the oxidized graphene with a solution containing an intercalant (e.g., tetrabutylammonium hydroxide) to form graphene oxide. The reaction between graphite and the oxidizing acid and the oxidant can be carried out at room temperature. An intercalant refers to a chemical capable of entering the space between graphene oxide. In some embodiments, treating the oxidized graphene with a solution containing an intercalant can be carried out at a temperature of at least about 60° C. (e.g., at least about 80° C.). Without wishing to be bound by theory, it is believed that washing the oxidized graphene with an aqueous solvent can remove the oxidizing acid, the oxidant, and any fully oxidized graphene that is soluble in water (which can include structural defects and therefore result in unstable graphene oxide). Further, without wishing to be bound by theory, it is believed that the graphene oxide formed by the above method can have significantly improved stability as it contains a much lower concentration of structural defects. In particular, a dispersion containing the graphene oxide thus formed can be stable over several months with minimal precipitation.

In some embodiments, the graphene derivative described herein can have an average particle size (e.g., particle length or width) of at least about 0.1 µm (e.g., at least about 0.5 µm, at least about 1 µm, at least about 5 µm, or at least about 10 µm) and/or at most about 100 µm (e.g., at most about 75 µm, at most about 50 µm, at most about 25 µm, or at most about 10 µm). In some embodiments, the graphene derivative described herein can have an average particle size (e.g., particle length or width) from at least about 1 µm to at least about 10 µm (e.g., about 5 µm).

In some embodiments, the graphene derivative described herein can have a large average aspect ratio (e.g., a ratio between length and thickness or a ratio between width and thickness). For example, the average aspect ratio of a graphene oxide can be at least about 50 (e.g., at least about 100 or at least 200) and/or at most about 500 (e.g., at most about 400 or at most about 300).

In general, the graphene derivative described herein (e.g., a graphene derivative containing a metal ion or a protein) can be used as a stationary phase in a separation technique. The separation technique includes column chromatography or batch chromatography.

In the embodiments of column chromatography, one can separate a protein of interest in a sample by first passing the sample through a stationary phase that selectively binds to the protein in a column (e.g., a metal or glass column) so that the protein is adsorbed onto the stationary phase, while the other components in the sample pass through the stationary phase. Subsequently, one can pass an eluent capable of desorbing the protein of interest from the stationary phase to collect the protein. Examples of column chromatography includes high performance liquid chromatography, ultra performance liquid chromatography, expanded bed adsorption chromatography, and fast protein liquid chromatography.

In the embodiments of batch chromatography, one can separate a protein of interest in a sample by first mixing the sample in a dispersion or suspension containing a stationary phase that selectively binds to the protein and a solvent (e.g., an aqueous solvent) in a container (e.g., a beaker) so that the protein is adsorbed onto the stationary phase. The protein-bound stationary phase can then be isolated from the other components in the sample by a suitable separation method, such as centrifugation, filtration, or decantation. The isolated stationary phase can then be washed with an eluent capable of desorbing the protein of interest from the stationary phase to recover the protein. Without wishing to be bound by theory, it is believed that the graphene derivative described herein can be used as a stationary phase in a chromatographic method to effectively isolate a protein from a sample while maintaining the biological activities of the protein. By contrast, although a conventional stationary phase material may be able to isolate a protein, it often deactivates the protein during the isolation process.

In general, depending on the pendant groups present in the graphene derivative described herein, the graphene derivative can be used as a stationary phase in chromatographic methods based on different separation mechanisms, such as size exclusion chromatography, hydrophobic interaction chromatography, ion-exchange chromatography, or affinity chromatography (e.g., immobilized-metal affinity chromatography (IMAC)).

In some embodiments, the graphene derivative containing a metal ion described above can be used as a stationary phase in IMAC to isolate or purify a tagged protein.

For example, graphene derivative 100 can be used as a stationary phase material to isolate a His-tagged protein (e.g., a His-tagged photosystem II core complex) from a sample in a batch IMAC by using the following method: One can first mix the sample with a dispersion or suspension containing graphene derivative 100 dispersed in a solvent (e.g., water) in a container (e.g., a beaker) so that the His-tagged protein is adsorbed onto graphene derivative 100 by forming a complex (e.g., through coordinative binding) between the metal ion (i.e., $Ni^2$) and the His tag in the protein. The protein-bound graphene derivative can then be separated from the other components in the sample by a suitable separation method, such as centrifugation, filtration, or decantation. The isolated graphene derivative can then be washed with an eluent capable of desorbing the His-tagged protein (e.g., an eluent containing imidazole or having a suitable pH (e.g., from about 3 to about 13)) from the protein-bound graphene derivative to recover the protein.

As another example, graphene derivative 100 can be used as a stationary phase material to isolate a His-tagged protein from a sample in a column IMAC by using the following method: One can first pass the sample through graphene derivative 100 in a column (e.g., a metal, glass, or plastic column) so that the protein is adsorbed onto graphene derivative 100 by forming a complex (e.g., through coordinative binding) between the metal ion (i.e., $Ni^2$) and the His tag in the protein. The other components in the sample that do not absorb onto graphene derivative 100 can be eluted out of the column Subsequently, one can pass an eluent capable of desorbing the His-tagged protein (e.g., an eluent containing imidazole or having a suitable pH) from the protein-bound graphene derivative to collect the His-tagged protein.

Other tagged proteins can be isolated in a manner similar to that described above by using suitable stationary phase materials (e.g., graphene derivatives containing suitable metal ions) and suitable eluents.

Graphene Derivatives Containing a Nanoparticle

Figure 2:
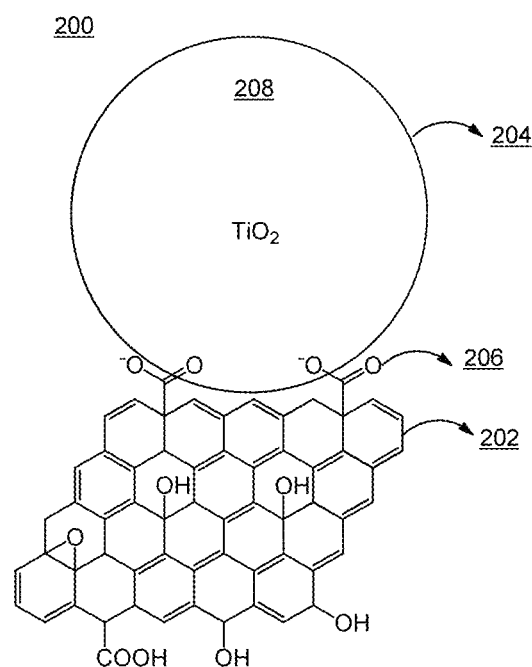
FIG. 2 is another embodiment of a graphene derivative containing a nanoparticle.

FIG. 2 illustrates an embodiment of a graphene derivative containing a nanoparticle. Specifically, referring to FIG. 2, a graphene derivative 200 includes a graphene core 202 and a pendant group 204. Pendant group 204 includes a linking group 206 and a nanoparticle 208 attached to the linking group (e.g., by covalent bonding). In some embodiments, linking group 206 can be a functional group (e.g., a carboxyl group) formed on a graphene oxide after the graphene oxide is prepared by oxidation. In some embodiments, linking group 206 can include a spacer group (e.g., $C_1$-$C_{20}$ alkylene). Examples of nanoparticle 208 include oxide nanoparticles (e.g., $SiO_2$ nanoparticles, metal oxide nanoparticles such as $TiO_2$ nanoparticles).

In some embodiments, a graphene derivative containing a nanoparticle can be prepared by (1) forming nanoparticles in a solvent, and (2) reacting the nanoparticles with a graphene oxide (by using native carboxyl groups on its surface or carboxyl groups generated by chemical functionalization of other oxygen-containing groups on the surface) to form a graphene derivative containing a nanoparticle. As a starting material, the graphene oxide can be in the form of a powder, a liquid-based composition (e.g., a suspension or a slurry), or a film. After the graphene derivative containing a nanoparticle is formed, excess reactants can be removed by the methods described above.

For example, a graphene derivative containing $TiO_2$ nanoparticles can be prepared by (1) forming $TiO_2$ nanoparticles by dispersing a $TiO_2$ precursor (e.g., a titanium salt such as titanium tetra-isopropoxide) in a solvent (e.g., an anhydrous alcohol) and (2) reacting the $TiO_2$ nanoparticles with carboxyl groups on a graphene oxide to form a graphene derivatives containing $TiO_2$ nanoparticles.

As another example, a graphene derivative containing $SiO_2$ nanoparticles can be prepared by (1) reacting $SiO_2$ nanoparticles (e.g., silica nanoparticles) with an amino-functionalized silane to form amino-functionalized $SiO_2$ nanoparticles, and (2) reacting amino-functionalized $SiO_2$ nanoparticles with a graphene oxide (which contains carboxyl groups) to form a graphene derivative containing $SiO_2$ nanoparticles. In some embodiments, the amino-functionalized silane can have the formula $NH_2$—R—$Si(OR')_3$, in which R is $C_1$-$C_{20}$ alkylene and R' is H or $C_1$-$C_{20}$ alkyl. An example of such a silane is aminopropyltriethoxysilane. In such embodiments, the $SiO_2$ nanoparticles are bonded to graphene core 202 through an amide group. In such embodiments, linking group 206 can have a formula —CO—NH—R—Si(—O—)$_3$, in which R is defined above.

In general, a graphene derivative containing a nanoparticle can be used as a stationary phase in a separation technique described herein (such as batch chromatography or column chromatography) to isolate or purify certain proteins. In some embodiments, a graphene derivative containing a $TiO_2$ nanoparticle can be used to isolate or purify phosphoproteins due to the high binding affinity between the $TiO_2$ nanoparticle and a phosphoprotein. Phosphoproteins include those containing phosphate groups esterified to an amino acid residue (e.g., serine, threonine, or tyrosine). Exemplary phosphoproteins include an Fc receptor, a Ulk antibody, a calcineurin, a K chromatin immunoprecipitate, or a urocotin.

For example, graphene derivative 200 can be used as a stationary phase material to isolate a phosphoprotein from a sample in a batch column chromatography by using the following method: One can first mix the sample with a dispersion or suspension containing graphene derivative 200 dispersed in a solvent (e.g., water) in a container (e.g., a beaker) so that the phosphoprotein is adsorbed onto graphene derivative 200 by binding between the phosphoprotein and the $TiO_2$ nanoparticle. The protein-bound graphene derivative can then be separated from the other components in the sample by a suitable separation method, such as centrifugation, filtration, or decantation. The isolated graphene derivative can then be washed with an eluent (e.g., a phosphate-buffered saline solution) capable of desorbing the phosphoprotein from the protein-bound graphene derivative to recover the phosphoprotein.

As another example, graphene derivative 200 can be used as a stationary phase material to isolate a phosphoprotein from a sample in a column chromatography by using the following method: One can first pass the sample through graphene derivative 200 in a column (e.g., a metal or glass column) so that the phosphoprotein is adsorbed onto graphene derivative 200 by binding between the phosphoprotein and the $TiO_2$ nanoparticle. The other components in the sample that do not adsorb onto graphene derivative 200 can be eluted out of the column. Subsequently, one can pass an eluent (e.g., a phosphate-buffered saline solution) capable of desorbing the phosphoprotein from the protein-bound graphene derivative to collect the phosphoprotein.

Other phosphoproteins can be isolated in a manner similar to that described above by using suitable stationary phase materials (e.g., graphene derivatives containing suitable nanoparticles) and suitable eluents.

In some embodiments, a graphene derivative containing a $SiO_2$ nanoparticle can be used as a reverse-phase stationary phase material. For example, such a graphene derivative can be reacted with alkylamines to form a material having a highly hydrophobic surface suitable for use in reverse-phase chromatography. Without wishing to be bound by theory, it is believed that a reverse-phase stationary phase material made from a graphene derivative containing a $SiO_2$ nanoparticle would have a significantly adsorption of the sample than a reverse-phase stationary phase material made from a conventional silica based material.

In some embodiments, a graphene derivative containing a $SiO_2$ nanoparticle can be further modified to include another type of nanoparticles (e.g., $TiO_2$ nanoparticles) by the methods described herein (e.g., by reacting at least some of the remaining carboxyl groups on the graphene core with $TiO_2$ nanoparticles) to form a graphene derivative containing two different types of nanoparticles. In such embodiments, the graphene derivative contains two different pendant groups, one containing a $SiO_2$ nanoparticle and the other containing a $TiO_2$ nanoparticle. Such a graphene derivative can be used to isolate or purify phosphoproteins.

In some embodiments, a graphene derivative containing a $SiO_2$ nanoparticle can be further modified to include a metal ion (e.g., $Ni^{2+}$) by the methods described herein (e.g., by reacting at least some of the remaining carboxyl groups on the graphene core with a compound having a nitrilotriacetic acid moiety and then with a metal salt such as $NiSO_4$) to form a graphene derivative containing both a nanoparticle and a metal ion. Such a graphene derivative can be used to isolate or purify tagged proteins (e.g., His-tagged proteins).

Without wishing to be bound by theory, it is believed that a graphene derivative containing $SiO_2$ nanoparticles and another type of nanoparticles or a metal ion can have improved permeability to an eluent when used in a column chromatography than a graphene derivative without any $SiO_2$ nanoparticle.

Graphene Derivatives Containing a Protein

In some embodiments, the graphene derivative described herein can include a protein in the pendant group (e.g., in pendant group 104 or 204 described above). The protein can be covalently bonded to the graphene core. Examples of such a protein include Protein A, Protein G, an E72G3 protein, or their derivatives. Such a graphene derivative can be used to isolate or purify antibodies.

In some embodiments, the graphene derivative can include a linking group between the graphene core and the protein. The linking group can be covalently bonded to the graphene core and covalently bonded to the protein. In some embodiments, the linking group can be an amide group (e.g., —CO—NH—). In other embodiments, the linking group can include a functional group, such as an acetamide moiety (e.g., an iodoacetamide or bromoacetamide moiety), a succinimide moiety (e.g., a N-hydroxysuccinimide moiety), a maleimide moiety (e.g., a N-hydroxysuccinimide moiety), or a thiosulfate moiety, or a chelating group complexed with a metal ion (such as those described above). For example, when the graphene derivative includes an iodoacetamide moiety in a pendant group, a suitable protein (e.g., a protein having binding affinity with an antibody) can be covalently bonded to the linking group by reacting the iodo group with the thiol group in a cysteine residue in the protein. In some embodiments, the linking group can include a spacer group (e.g., $C_1$-$C_{20}$ alkylene).

In general, a graphene derivative containing a protein can be prepared by methods described herein or methods known in the art. For example, a graphene derivative containing Protein A can be prepared by mixing a graphene derivative containing a metal ion (e.g., $Ni^{2+}$ or $Co^{2+}$) described above (e.g., in a dispersion or a film) with a His-tagged Protein A so that the His-tagged Protein A is bound to the metal ion. As another example, a graphene derivative containing Protein A can be prepared by (1) optionally activating the carboxyl groups on a graphene oxide (e.g., by using NHS and EDC) dispersed in an aqueous solvent or in the form of a film, (2) reacting the optionally activated graphene oxide with the primary amine groups on Protein A to covalently bond Protein A to the graphene core through an amide group (e.g., —CO—NH—). As another example, a graphene derivative containing a protein (e.g., Protein A) can be prepared by (1) treating a graphene oxide with 4-(maleimido)phenyl isocyanate or 4-(chloromethyl) phenyl to react the hydroxyl groups on the graphene oxide's surface with phenyl isocyanate end of the molecule, and (2) reacting the maleimide moiety in the graphene derivative thus formed with a thiol group in the protein (e.g., a thiol group in a cysteine residue in the protein) to form a graphene derivative containing a covalently bonded protein.

In general, a graphene derivative containing a protein can be used as a stationary phase in a separation technique described herein (such as batch chromatography or column chromatography). For example, a graphene derivative containing Protein A can be used as a stationary phase in an immunoaffinity chromatography (either as a batch chromatography or as a column chromatography) to isolate or purify antibodies through the binding between Protein A and the Fc region of the antibodies. Without wishing to be bound by theory, it is believed that the graphene derivative containing Protein A can have a significantly higher antibody loading capacity than a conventional Protein A stationary phase material.

For example, a graphene derivative containing a protein can be used as a stationary phase material to isolate an antibody from a sample in a batch immunoaffinity chromatography by using the following method: One can first mix the sample with a dispersion or suspension containing a graphene derivative containing a protein dispersed in a solvent (e.g., water) in a container (e.g., a beaker) so that the antibody of interest is adsorbed onto the graphene derivative by binding between the antibody and the protein on the graphene derivative. The antibody-bound graphene derivative can then be separated from the other components in the sample by a suitable separation method, such as centrifugation, filtration, or decantation. The isolated graphene derivative can then be washed with an eluent (e.g., a buffer solution containing EDTA and glycerol and having a pH of about 8) capable of desorbing the antibody from the antibody-bound graphene derivative to recover the antibody.

As another example, a graphene derivative containing a protein can be used as a stationary phase material to isolate an antibody from a sample in a column immunoaffinity chromatography by using the following method: One can first pass the sample through the graphene derivative in a column (e.g., a metal or glass column) so that the antibody is adsorbed onto the graphene derivative by binding between the antibody and the protein on the graphene derivative. The other components in the sample that do not absorb onto the graphene derivative can be eluted out of the column Subsequently, one can pass an eluent (e.g., a buffer solution containing EDTA and glycerol and having a pH of about 8) capable of desorbing the antibody from the antibody-bound graphene derivative to collect the antibody.

Graphene Derivatives Containing a Functional Group

In some embodiments, the graphene derivative described herein can include a functional group in the pendant group (e.g., pendant group 104 or 204 described above). Exemplary functional groups include a sulfonate group, an amine group, a quaternary ammonium group, or a chelating group. For example, the pendant group can include —CO—NH—R—$SO_3H$, —CO—NH—R—$N(R'R''R''')^+$, —CO—NH—R—N(R'R''), —CO—NH—R—SH, —CO—NH—R—COOH, —CO—NH—R—$N(CH_2COOH)_2$, —CO—NH—R—NH—R—$PO_3H$, or an EDTA derivative, in which each R, independently, is $C_1$-$C_{20}$ alkylene, and each of R', R'', and R''', independently, is H or $C_1$-$C_{20}$ alkyl. In another embodiment, the pendant group can include —(CO)$_x$—NH—R—$SO_3H$, —(CO)$_x$—NH—R—$N(R'R''R''')^+$, —(CO)$_x$—NH—R—N(R'R''), —(CO)$_x$—NH—R—SH, —(CO)$_x$—NH—R—COOH, —(CO)$_x$—NH—R—$N(CH_2COOH)_2$, —(CO)$_x$—NH—R—NH—R—$PO_3H$, or an EDTA derivative, wherein x is 0 or 1; each R, independently, is $C_1$-$C_{20}$ alkylene; and each of R', R'', and R''', independently, is H or $C_1$-$C_{20}$ alkyl.

In general, a graphene derivative containing a functional group can be prepared by methods described herein or methods known in the art. For example, a graphene derivative containing a sulfonate group can be prepared by reacting a graphene oxide (which contains carboxyl groups) dispersed in an aqueous solvent or in the form of a film with a compound containing both a primary amine group and a sulfonate group so that the compound is covalently bonded to the graphene core through an amide group. As another example, a graphene derivative containing an EDTA derivative (i.e., a chelating group) can be prepared by reacting an EDTA with an amino group introduced on the graphene core or by reacting an EDTA radical with a vinyl group introduced on the graphene core. The amino group can be introduced on the graphene core by, e.g., (1) reacting ethylenediamine with a carboxyl group on a graphene oxide to form a graphene derivative containing a —(CO)—NH—$CH_2CH_2$—$NH_2$ group or (2) reacting sulfonyl chloride with a carboxyl group on a graphene oxide to form a graphene oxide containing a —C(O)Cl group and then reacting the graphene oxide thus formed with the ethylenediamine to form a graphene derivative containing a —(CO)—NH—$CH_2CH_2$—$NH_2$ group or (3) by reacting the amino group with epoxyde groups on the surface of graphene oxide. Subsequently, the graphene derivative containing an amino group thus formed can react with a carboxyl group on EDTA to form a graphene derivative containing an EDTA moiety. The vinyl group mentioned above can be introduced on the graphene core by, e.g., reacting a compound containing a vinyl group and an amino group with a carboxyl group on the graphene core. An EDTA radical can be formed by, e.g., reacting a EDTA sodium salt with a Ce(IV) salt to form an EDTA radical [$(NaO_2CCH_2)_2N\dot{C}(H)CH_2N(CH_2CO_2NO_2)$]. Subsequently, the graphene derivative containing a vinyl group thus formed can react with the EDTA radical above to form a graphene derivative containing an EDTA moiety. Graphene derivatives containing other functional groups described herein can be prepared by similar methods.

In general, a graphene derivative containing a functional group can be used as a stationary phase in a separation technique described herein (such as batch chromatography or column chromatography). For example, such a graphene derivative can be used as a stationary phase of an ion-exchange chromatography. In some embodiments, a graphene oxide containing native carboxyl groups (i.e., without further chemical modifications) can also be used as a station phase of an ion-exchange chromatography.

While certain embodiments have been disclosed, other embodiments are also possible.

In some embodiments, when the graphene derivative described herein is used as a stationary phase in column chromatography, the stationary phase can further include a spacer (e.g., an inert spacer) mixed with the graphene derivative. Examples of suitable spacers include oxides (e.g., metal oxides or transition metal oxides) and polymers. An example of a spacer is silica (e.g., $SiO_2$ particles or nanoparticles). Without wishing to be bound by theory, it is believed that, since the graphene derivative described herein can have a high aspect ratio, it can result in a tight packing when used as a stationary phase in a column and therefore become impermeable to the mobile phase (especially when the mobile phase elutes at atmospheric pressure through the column). Including a spacer in the stationary phase could make it a more permeable than a stationary phase without such a spacer.

In another embodiment, graphene derivatives may be used in a device for producing hydrogen. The graphene derivatives may be modified so that the first pendant group comprises a first linking group attached to the graphene core and a photocathode nanoparticle, and the second pendant group comprises a second linking group attached to the graphene core and a photoanode nanoparticle. The graphene derivative may be suspended.

Preferably, the first and second linking groups include a nitrilotriacetic acid moiety. In another preferred aspect, the first pendant group further includes a metal ion coordinated with the first linking group and the second pendant group further includes a second metal ion coordinated with the second linking group. $Ni^{2+}$ is the preferred ion for the first and second pendant groups. Preferably, the first photocathode nanoparticle includes a first His-tagged protein binding to the first metal ion and the photoanode nanoparticle includes a second His-tagged protein binding to the second metal ion. The first His-tagged protein preferably includes a His-tagged photosystem I core complex and the second His-tagged protein includes a His-tagged photosystem II core complex. The first pendant group may further include a platinum nanoparticle or a hydrogenase. The platinum nanoparticle may be bonded to the His-tagged photosystem I core complex with, for example, the following: —S—$(CH_2)_6$—S—.

Preferably, the photocathode includes a first semiconductor and the photoanode includes a second semiconductor. The first semiconductor may be coated with a catalyst for a hydrogen evolving reaction and the second semiconductor may be coated with a catalyst for an oxygen evolving reaction.

The device for producing hydrogen may include first and second transport layers; a first graphene layer including a first graphene derivative, the first transport layer between the first graphene layer and the second transport layer; and a second graphene layer including a second graphene derivative, the second transport layer between the first transport layer and the second graphene layer.

The first graphene derivative includes a first graphene core and a first pendant group, the first pendant group includes a first linking group covalently bonded to the first graphene core, a first metal ion coordinated with the first linking group, and a first His-tagged protein binding to the first metal ion.

Similarly, the second graphene derivative includes a second graphene core and a second pendant group, the second pendant group including a second linking group covalently bonded to the second graphene core, a second metal ion coordinated with the second linking group, and a second His-tagged protein binding to the second metal ion.

Each of the first and second linking groups includes a nitrilotriacetic acid moiety. Each of the first and second metal ions is $Ni^{2+}$. The first His-tagged protein includes a His-tagged photosystem I core complex and the second His-tagged protein includes a His-tagged photosystem II core complex.

Preferably, each of the first and second transport layers includes a polyaniline or a sulfonated polyaniline Preferably, the molar ratio between the His-tagged photosystem II core complex and the His-tagged photosystem I core complex is 2:1.

The first pendant group may further include a platinum nanoparticle or a hydrogenase. The platinum nanoparticle may be bonded to the His-tagged photosystem I core complex with, for example, the following: —S—$(CH_2)_6$—S—.

The device may further include first and second housings, wherein the first housing, together with the first transport layer, defines a first compartment and the second housing, together with the second transport layer, defines a second compartment. Preferably, the first graphene layer is disposed in the first compartment and the second graphene layer is disposed in the second compartment.

The contents of all publications cited herein (e.g., patents, patent application publications, and articles) are hereby incorporated by reference in their entirety.

The following examples are illustrative and not intended to be limiting.

EXAMPLE 1

Preparation of Graphene Derivative Containing Nickel Ions

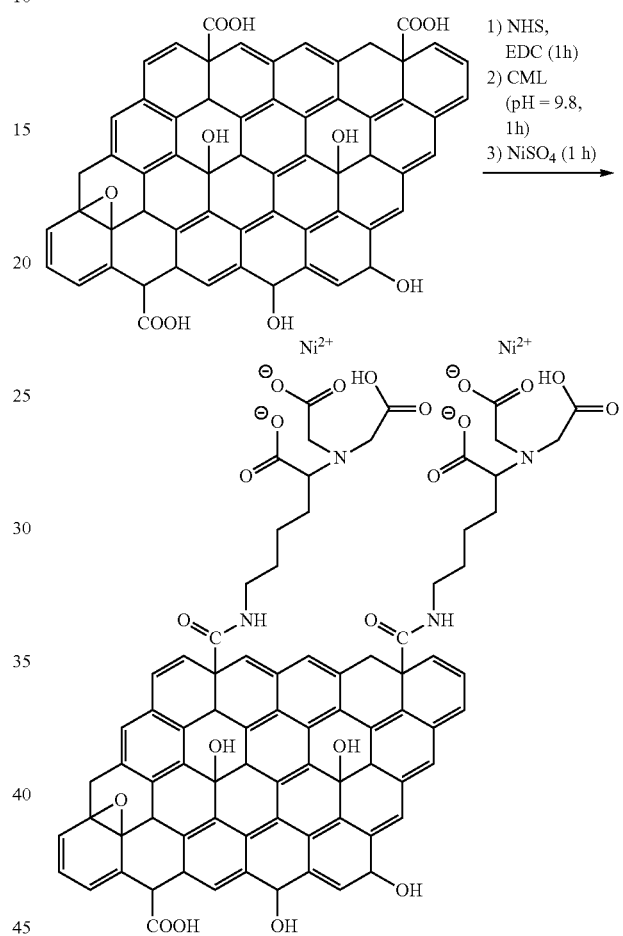

A graphene derivative containing nickel ions was prepared as follows: The starting material was a suspension containing graphene oxide (GO) with oxygen content between 8 mol % and 35 mol % provided by the Nano-materials and Devices Group at Rutgers University. The entire preparation process was conducted at room temperature. Specifically, 10 mL of a slurry containing 15-20 vol % GO was treated for 1 hour with a 10 mL solution containing 10 mM N-hydroxysuccinimide (NHS) and 10 mM N-ethyl-N'-(3-dimethylaminopropyl)-carbodiimide, both of which were in excess to the carboxyl groups on the GO. After the suspension was then centrifuged at 21,000×g for 5 minutes, the precipitate was washed with ultra-pure water to form a graphene derivative containing activated carboxyl groups. The washed precipitate was then treated for 1 hour with an excess (10 mL) of a 150 mM $N_\alpha,N_\alpha$-bis(carboxymethyl)-L-lysine hydrate (pH=9.8) solution. After the suspension was centrifuged at 21,000×g for 5 minutes again, the precipitate was washed with ultra-pure water to provide a graphene derivative containing a nitrilotriacetic acid moiety. The washed precipitate was subsequently treated with an excess (10 mL) of a 100 mM solution of $NiSO_4$ to provide a graphene derivative containing nickel ions (i.e., GO-Ni-NTA). The resultant resin was stored as a wet precipitate at 4° C. for further use.

It was determined by EPR spectroscopy that the reaction step involving $N_a,N_a$-bis(carboxymethyl)-L-lysine at pH of 9.8 produced an unexpected increment of the carboxylic groups onto GO, beyond the level of the carboxylic group that would have been formed based on the reaction between $N_a,N_a$-bis(carboxymethyl)-L-lysine and the carboxyl group present in the starting GO. Without wishing to be bound by theory, it is believed that this was due to a direct reaction of $N_a,N_a$-bis(carboxymethyl)-L-lysine with the epoxy groups on the surface of the starting GO. As a result, additional Ni-NTA functional groups can be formed on the surface of GO.

EXAMPLE 2

Immobilization of PSII Core Complexes onto GO-Ni-NTA IMAC Resin in a Suspension A Photosystem II core complex (PSII CC) protein that was His-tagged on the protein domain CP47 was isolated by a standard protocol from a thermophilic cyanobacterium *Thermosynechococcus elongatus*. The PSII CC protein is a dimeric protein with a physical dimension of 20.5 nm (L)× 11.0 nm (W)×10.5 nm (D) and a molecular weight of 680 kDa. The His-tagged PSII CC protein was incubated in a suspension containing the GO-Ni-NTA resin prepared in Example 1 for 20 to 60 minutes.

Flow cytometry was used to verify coordination of the PSII CC protein to the resin and to measure the protein loading capacity of the resin. Flow cytometry allows real time and simultaneous measurements of fluorescence at 692 nm (including side scattering (SSC) and forward scattering (FSC)) using an interrogating laser at 488 nm Individual particles undergo hydrodynamic focusing in the presence of a sheath fluid. SSC and FSC are proportional to the size of the particles depending on the orientation of the particles with respect to the interrogating laser. It was shown that graphene derivative particles in the suspension tended to align themselves in the presence of the resulting Newtonian fluid. The flow cytometer detected systematically individual graphene derivative particle, revealing a high aspect ratio typical of 2D structures. The interaction between the PSII CC protein molecules and GO-Ni-NTA particles was revealed by the analysis of fluorescence versus SSC.

Figure 3:
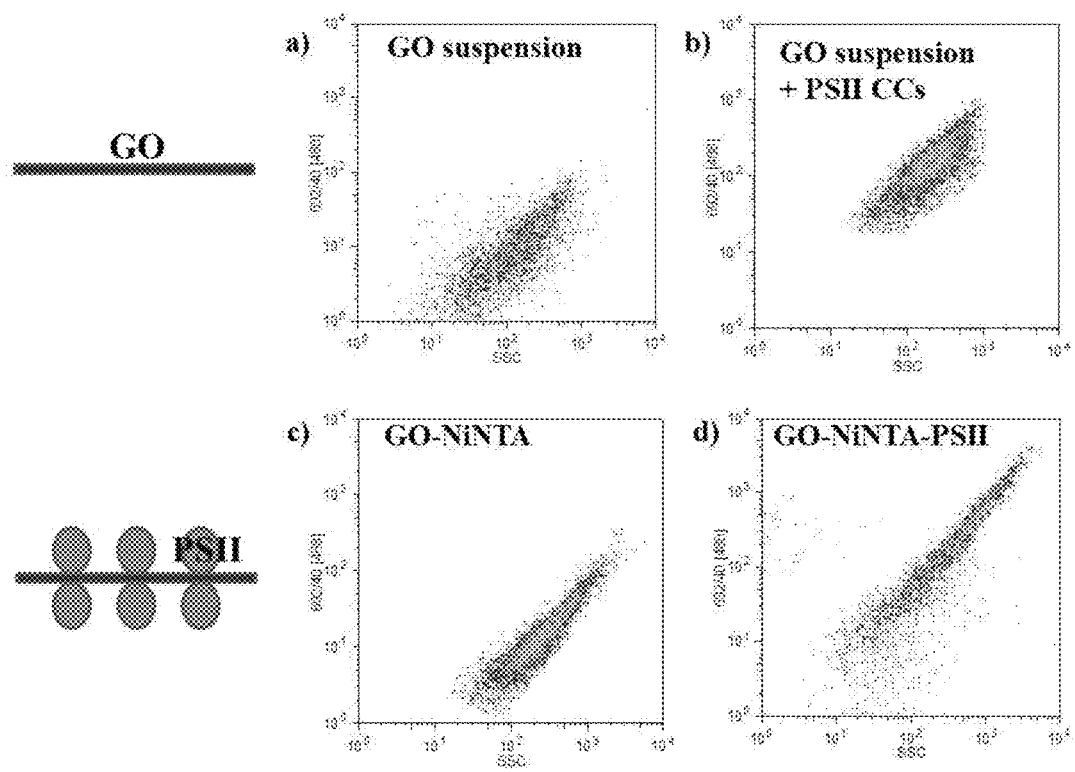
FIGS. 3A-3D are graphs illustrating the flow cytometry intensities of pristine GO and GO-Ni-NTA in the absence and presence of a PSII CC protein obtained in Example 2.

Specifically, flow cytometry was used to measure the fluorescence intensities of four samples, i.e., (1) unmodified GO particles, (2) GO-Ni-NTA particles, (3) unmodified GO particles in the presence of the above PSII CC protein, and (4) GO-Ni-NTA particles in the presence of the above PSII CC protein. The results are summarized in FIG. 3. As shown in FIG. 3, the fluorescence intensity of the unmodified GO particles was less than that of the unmodified GO particles in the presence of the PSII CC protein. Without wishing to be bound by theory, it is believed that there is a moderate level of correlation between fluorescence of the unmodified GO particles in the presence of PSII CC protein and its SSC possibly due to non-specific hydrophobic and/or hydrophilic interaction between the PSII CC protein molecules and the amphiphilic unmodified GO particles. Similarly, the fluorescence intensity of the GO-Ni-NTA particles was less than that of GO-Ni-NTA particles in the presence of the PSII CC protein. Without wishing to be bound by theory, it is believed that the His-tagged PSII CC protein coordinated with the nickel ion in the Ni-NTA groups on the GO-Ni-NTA particles. The high level of linear correlation between fluorescence of GO-Ni-NTA-PSII and its SSC demonstrated an increased protein loading onto the GO-Ni-NTA particles.

Protein loading capacity of the GO-Ni-NTA particles obtained from Example 1 was measured as follows: A GO-Ni-NTA particle suspension (solution A) was prepared by 1-to-10 dilution of a GO-Ni-NTA slurry having a GO-Ni-NTA volume fraction of 15-20%. The dilution buffer contained 20 mM MES, 10 mM $MgCl_2$, 10 mM $CaCl_2$ and 0.03% (w/v) β-dodecylmaltoside. The protein concentration of a PSII CC stock solution was determined by two independent methods, i.e., (1) a Chlorophyll a (Chl a) assay and (2) an amino acid analysis. A PSII CC stock suspension (0.93 mg Chl a/mL or 2,5646 mg of protein/mL) was diluted 1-to-10 using the same buffer mentioned above to form solution B. 5 µL of solution A was added to increasing volumes (from 0 to 32 µL) of solution B. The above buffer was added in each case up to 450 µL total volume. After each mixture was incubated for 1 hour, each mixture was centrifuged at 21,000×g for 5 minutes at room temperature. The precipitate was washed in 1 mL of the above buffer, followed by centrifugation at 21,000×g for 5 minutes at room temperature. The washing and centrifugation were repeated three times. The precipitate thus formed was re-suspended with the above buffer up to form a suspension having a volume of 450 µL. Each suspension was probed by flow cytometry. The results showed that the fluorescence intensity of the particles at 692 nm increased initially and then reached a certain maximum value, indicating that the PSII CC protein molecules were adhered to the GO-Ni-NTA particles approaching a maximum protein loading. The protein loading of the GO-Ni-NTA particles obtained from Example 1 was determined to be about 410-552 mg of the PSII CC protein per mL of the GO-Ni-NTA particles based on the Chl a assay or 82-109 mg of the PSII CC protein per mL of the GO-Ni-NTA particles based on the amino acid analysis. The discrepancy between the Chl a assay and the amino acid analysis is believed to be due to the lower accuracy of the former assay. By contrast, the highest protein loading capacity known in the art (e.g., as shown in a commercial product from Thermo Scientific, i.e., HISPUR Ni-NTA resin) is 60 mg of His-tagged protein per mL of the resin.

The GO-Ni-NTA resin was shown to stabilize the PSII CC protein quite effectively. In order to assess this stability enhancement, the quantum yield of photochemistry ($F_v/F_m$) of the PSII CC protein anchored to GO-Ni-NTA in an aqueous buffer (20 mM MES, 10 mM $MgCl_2$, 10 mM $CaCl_2$ and 0.03% (w/v) β-dodecylmaltoside) at ambient temperature was monitored. The $F_v/F_m$ values were 0.250 and 0.264 and after 25 and 37 minutes, respectively. These results indicated that no detectable inactivation of the PSII CC protein occurred during the time of measurement, while an isolated PSII CC protein typically becomes inactive in the same aqueous buffer under the same conditions. In other words, these results indicated that the PSII CC protein was compatible with the GO-Ni-NTA resin and was appreciably stabilized by it. This stabilization effect is advantageous for the purpose of chromatographic isolation of biologically active proteins such as a PSII CC protein.

The approach described above can be used for proteins other than PSII CCs. In particular, similar results were obtained using green fluorescent protein derivatives, such as mCherry fluorescent protein, mOrange fluorescent protein, and dimeric tdTomato fluorescent protein. These proteins exhibited retention of their fluorescence spectra throughout the chromatographic isolation procedure, indicating conservation of protein folding after isolation.

EXAMPLE 3

Immobilization of PSI Core Complex Protein onto GO-Ni-NTA Thin Film

The functionalization with Ni-NTA groups was performed directly on top of a 1 cm² Au-coated silicon support further coated with GO with an oxygen content between 8 and 35 wt % (i.e., Si—Au-GO support). The surface treatment process was conducted at room temperature. Specifically, the Si—Au-GO support was treated for 1 hour with an excess (3 mL) of a 10 mM N-hydroxysuccinimide (NHS) and 10 mM N-ethyl-N'-(3-dimethylaminopropyl)carbodiimide solution to activate the carboxyl groups on the GO. After the activated Si—Au-GO support was washed three times with ultra-pure water, it was treated for 1 hour with an excess (3 mL) of a 150 mM $N_a,N_a$-bis(carboxymethyl)-L-lysine hydrate (pH=9.8) solution. The Si—Au-GO support thus formed was washed three times again with ultra-pure water to provide a support containing GO having a nitrilotriacetic acid moiety. The washed support was then treated with an excess (3 mL) of a 100 mM solution of $NiSO_4$ to form a support containing GO having nickel ions. Functionalization at the different steps was confirmed by FT-IR Attenuated Total Reflectance spectroscopy. The resulting $Ni^{2+}$-NTA-coated support (Si—Au-GO-Ni-NTA) was used immediately for protein isolation.

A PSI CC protein was isolated from *Synechococcus* sp. 7002 by standard procedures. The structure of the PSI CC protein from *Synechococcus* sp. 7002 is similar to that of the PSI CC protein form *Synechococcus elongatus*, whose structure has been resolved at atomic level by x-ray crystallography. The PSI CC protein thus obtained had a trimeric structure. The cylindrical trimer had a diameter of about 22 nm and a height of about 10 nm. The adhesion of the PSI CC protein to the GO-Ni-NTA particles was confirmed by Atomic Force Microscopy. The features detected on the surface of the Au substrate appeared to be dimers of trimers.

EXAMPLE 4

Comparison in Protein Loading Capacity Between GO-Ni-NTA and Two Commercial Resins The protein loading capacities of the GO-Ni-NTA resin prepared in Example 1 and two commercial resins, namely Life Technologies Probond Ni-NTA resin and Qiagen Ni-NTA resin, were measured using a PSII CC protein following the procedures below: The protein loading capacities were obtained using a 1.5 μL aliquot of the GO-Ni-NTA resin and 5 μL aliquots of the commercial resins. PSII CC protein loading capacities of the resins were determined indirectly by UV-Visible spectroscopy using a NanoDrop 1000 spectrophotometer at 680 nm UV-Visible spectra were collected on the PSII CC protein solutions before and after treatment with the resins and after elution with imidazole. Protein samples were incubated in batch mode with each of the resins at 4° C. for 1 hour on a rotisserie. Incubation was carried out in a 40 mM MES pH 6.5 buffer supplemented with 15 mM $MgCl_2$, 15 mM $CaCl_2$, 20% glycerol and 1M Betaine. Protein-resin samples were spun at 4° C. for 5 minutes at 21,000 xg. The protein loaded resins were then subjected to washing and elution steps. After each step protein samples were spun at 4° C. for 5 minutes at 21,000 xg. Resins were washed with 480 uL of the buffer described above prior to elution. Elution was performed on ice (for the GO-Ni-NTA resin) or 4° C. on a rotisserie (for the two commercial resins) using 150 mM MES pH 6.5 buffer supplemented with 15 mM $MgCl_2$, 15 mM $CaCl_2$, 200 mM NaCl, 0.1% (w/v) Dodecyl Maltoside, 300 mM Imidazole, 10% (w/v) glycerol and 1M Betaine.

Figure 4:
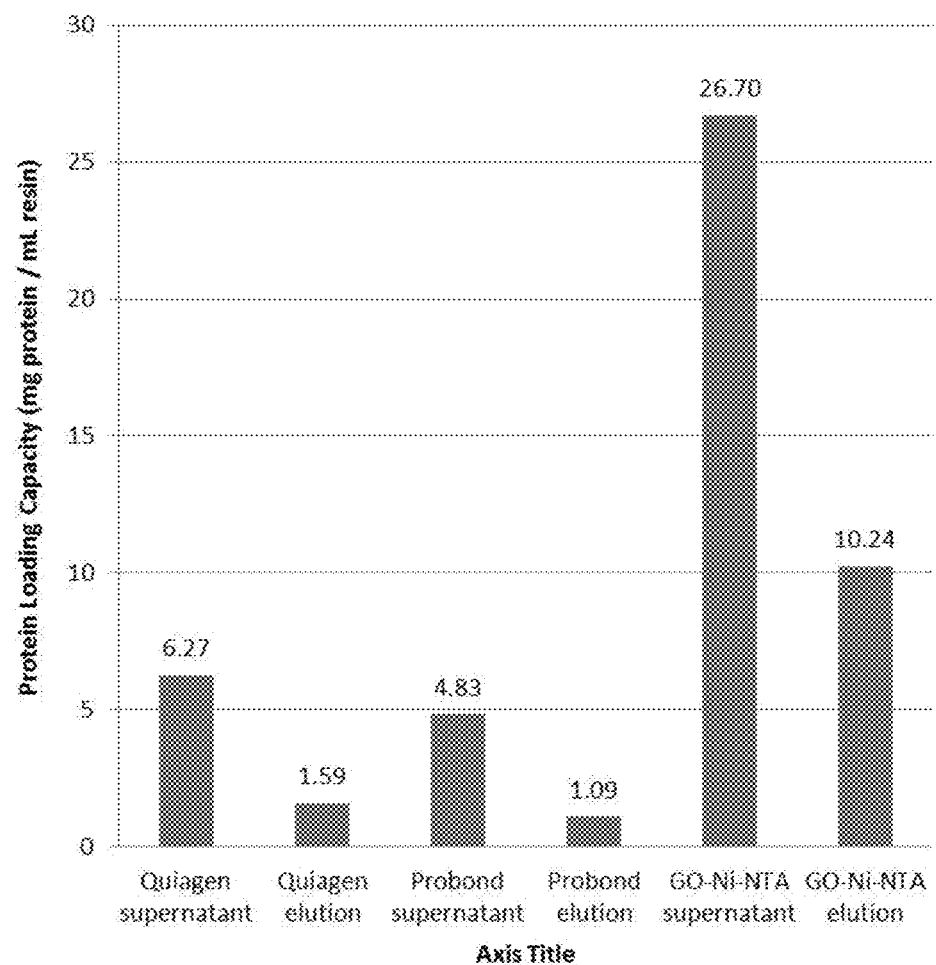
FIG. 4 is a graph illustrating the PSII CC protein loading capacities of GO-Ni-NTA and two commercial resins obtained in Example 4.

The results of the above tests are summarized in FIG. 4, which shows the protein loading capacities calculated based on the difference of the amounts of protein left in the supernatant before and after incubation with each resin and based on the amount of protein recovered from the resin after elution with imidazole. As shown in FIG. 4, the GO-Ni-NTA resin unexpectedly exhibited a PSII CC protein loading capacity 5-10 times as high as the protein loading capacities of the two commercial resins tested under the same purification conditions.

EXAMPLE 5

Functionalization of GO Suspended Particles with Ni-NTA Groups

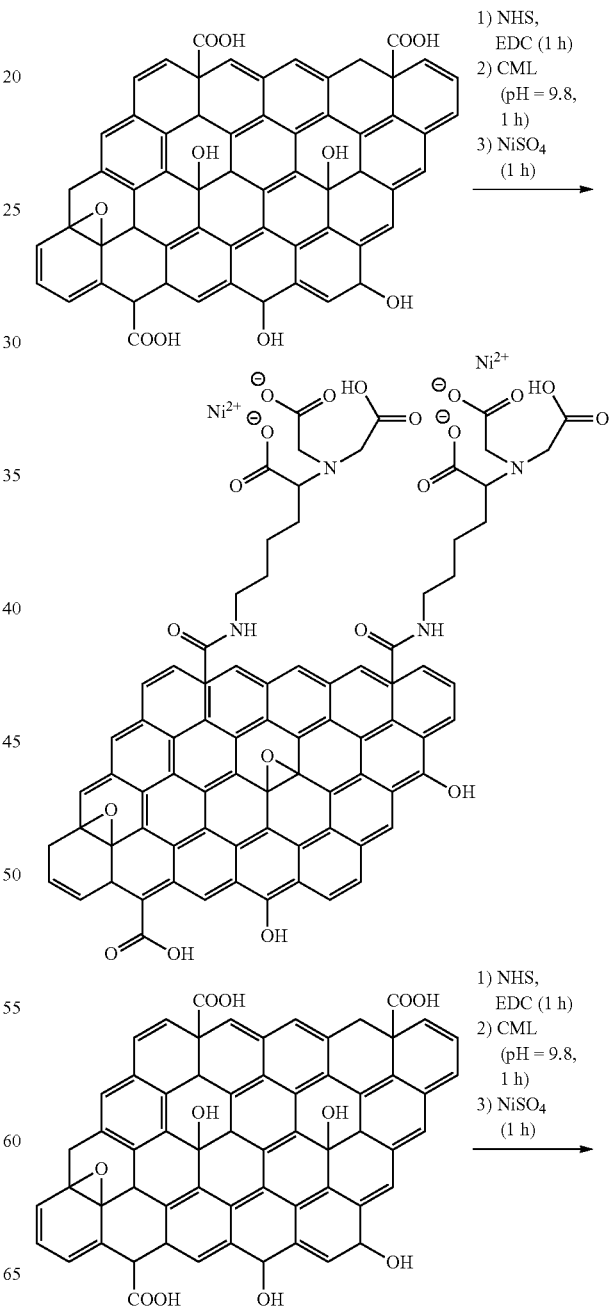

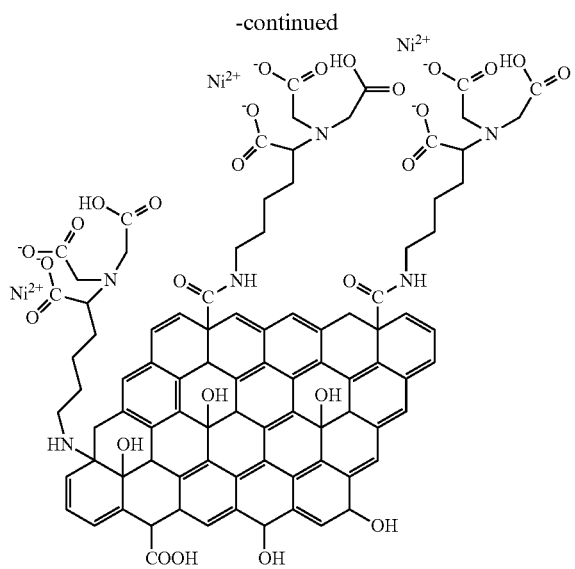

EXAMPLE 6

Directional Immobilization of PSII and PSI CCs onto GO Single-Layers and Thin Films Embodiments for the photoelectrochemical systems require the immobilization of PSII CCs on the stroma side and PSI CCs on the luminal side onto GO. See below. The His-tagged PSII and PSI CCs are linked to GO, the stroma side of PSII and luminal side of PSI. The use of His-tagged CCs makes the binding task to a $Ni^{2+}$-NTA-GO, relatively straightforward both on GO single layers and onto thin films. Similarly it is possible to attach His-tagged PSI-CC-Pt and PSI-CC-HG (HG=hydrogenase). PSI-CC-Pt consists of PSI CCs wired to Pt (considered in the following) or PSI CCs platinized on the acceptor side, or PSI CCs bearing Pt nanoparticles on the acceptor side. PSI-CC-HG consists of PSI CCs wired to hydrogenases. Monolayers of each CCs are obtained by controlling concentration levels of the CCs. By this method it is possible to attach simultaneously PSII and PSI CCs or PSI-CC-Pt or PSI-CC-HG bio-conjugates. In the case of GO in suspension it is possible to use only oxygen-insensitive HG, because HG is not be shielded against oxygen evolving at the water oxidizing complex (WOC) of PSII CCs.

Photoelectrochemical Hydrogen Production Based on PSII/PSI Photosynthetic Core Complexes: The Principles Energetics of a Photoelectrochemical System for Hydrogen Generation ($H_2$-PES) based on PSII/PSI/Pt/GO The synthesis of hydrogen from water requires energy and reducing power (low-potential electrons). FIG. 5 shows a viable electron pathway from water to hydrogen gas on the redox midpoint potential energy (RMPE) scale, involving both the photosynthetic PSII and PSI CCs, GO and Pt NP. For the sake of comparison the vacuum energy level is also indicated. Both scales are in eV. On the basis of the Nernst equation it is possible to evaluate the pH dependence of both water oxidation and proton reduction semi-reactions. Both these semi-reactions occur at moderate acidic conditions. pH=4 is a reasonable assumption, therefore $H_2O \rightarrow \frac{1}{2}O_2 + 2H^+ + 2e^-$ and $2H^+ + 2e^- \rightarrow H_2$ (Pt) (hydrogen electrode semi-reaction) are indicated at 1.0 eV and -0.24 eV, respectively. At pH=7 the RMPE for hydrogen generation is -0.41 eV; at pH=4 it is -0.24 eV. Possible physical structures for viable systems, described so far from energetic perspective, are presented in the following section.

Embodiment 1: A $H_2$-PES Based on PSII/PSI onto GO Single-Layers in Aqueous Suspensions As described above it is possible to simultaneously attach PSII CCs and PSI-CC-Pt directly onto single layers of GO in aqueous suspension. Such a system readily generates hydrogen. A similar system is assembled from PSII CCs and PSI-CC-HG, using oxygen tolerant hydrogenases. In both these types of systems every suspended layer of GO becomes a fully functional and independent photoelectrochemical system for hydrogen generation in which GO represents the electronic connection between PSII and PSI CCs. The use of redox mediators is still a possible alternative. The control of the pH is important. Unlike a galvanic system in which PSII and PSI are located in separate compartments, it is not possible to buffer PSII and PSI at different pH values. There is an optimum pH at which both PSII and PSI CCs can operate simultaneously. The optimum pH value is about 6. Indeed it was previously shown that PSI-CC-Pt bio-conjugates generate hydrogen at their maximum efficiency at pH=6. If precipitation issues of the CC-GO particles arise a mixture of PEO in water as a solvent is used. The PEO content allows modulation of the viscosity. The use of detergents like Ficolli is also possible.

Hydrogen Generation Efficiency of a Hybrid Photosynthetic GO Suspension

As explained above, GO can be synthesized with oxygen varying between 8% and 35%. In all concentration ranges, there are enough COOH groups on the surface that a full coverage of core complexes on both sides of a GO flake is expected. In the following calculation, it can be assumed that the average GO flake is circular and has an average diameter of 5 μm. The surface area of one face is 20 μm². The total area is 40 μm². The rectangular footprint of a PSII CC dimer is 20.5 nm (L)×11.0 nm (W) or $2.26 \times 10^{-4}$ μm². The square footprint of a PSI CC trimer (a circle approximately 22 nm in diameter) is 22 nm×22 nm or $4.84 \times 10^{-4}$ mm². It can be assumed for simplicity that a PSI trimer and 2 PSII dimers occupy the same area ($4.84 \times 10^{-4}$ mm²). If each face is covered with PSII-CC/PSI-CC-Pt mixture in a 2:1 ratio, it can be expected 2 PSII CCs every PSI-CC-Pt. Cumulatively on the available surface of a single GO flake, there will be 41300 PSI-CC-Pt trimers (or 123,900 PSI-CC-Pt monomers) and 82,600 PSII-CC dimers (or 165,200 PSII-CC monomers). If it is assumed that the PSII CCs will be able to deliver a current density of 14 μA/cm² under low light conditions (100 μmol quanta·m$^{-2}$·s$^{-1}$), on each flake a current of $2.8 \times 10^{-6}$ μA will be available for hydrogen generation. Since each PSI is very efficient in the conversion of hydrogen and there is more than one PSII-CC monomer per PSI-CC-Pt monomer, it can be assumed that all this current will be entirely converted to hydrogen gas. If it is assumed that the C—C bond is 1.4207 Å and that a GO flake is circular, then each GO flake contains at the least $3 \times 10^9$ C atoms (estimated on the basis of exploratory DFT computations). In the case of 8%-oxygen GO along with the $3 \times 10^9$ C atoms, there are at least $2.4 \times 10^8$ O atoms for a total mass of $6.6 \times 10^{-14}$ g. If it is assumed that there is a 1 L GO suspension of 2.5 mg/mL or 2.5 g/L (a fair assumption in the case of 8%-oxygen GO), then there are $3.8 \times 10^{13}$ GO flakes per liter. Therefore, all the flakes in a liter could generate 110 A for hydrogen generation, which correspond to $5.7 \times 10^{-4}$ mol $H_2$ per second per liter of suspension. Similarly, in the case of 35%-oxygen GO, along with the $3 \times 10^9$ C atoms, there are at least $1 \times 10^9$ O atoms for a total mass of $8.6 \times 10^{-14}$ g. If it is assumed that there is a 1 L GO suspension of 5 mg/mL or 5 g/L (a fair assumption in the case of 35%-oxygen GO), than there are $5.8 \times 10^{11}$ GO flakes per liter. Therefore, all the flakes in a liter could generate 160 A for hydrogen generation, which correspond to $8.3 \times 10^{-4}$ mol $H_2$ per second per liter of suspension. Considering that hydrogen generation occurs across a potential difference of about 1.2 V, it can be calculated that the power output of just 1 liter of photosynthetic GO suspension is 130 W for 8%-oxygen GO and 190 W for 35%-oxygen GO. If a quantum efficiency factor of 10% (see following section) is applied, then it would be possible to obtain 13 W or $5.7 \times 10^{-5}$ mol $H_2$ per second per liter of suspension for 8%-oxygen GO and 19 W or $8.3 \times 10^{-5}$ mol $H_2$ per second per liter of suspension for 35%-oxygen GO. In half an hour, 0.10 mol of $H_2$ per liter of suspension for 8%-oxygen GO and 0.15 mol of $H_2$ per liter of suspension for 35%-oxygen GO would be produced. Similar calculations could be performed with HG in the place of Pt NP, and the expected yields are even higher. If it is assumed a power output of 10 W per liter, an Olympic-size pool (2,500,000 L) will correspond to a power output of 25 MW.

The benefit of the increment of area permitted by the direct use of GO flakes is evident from the calculations above. The expected flow of hydrogen is quite high, and PSII and PSI can hardly be expected to survive long under such a reducing environment. Still, the benefit of a demonstration that $H_2$-generation onto GO is feasible, is relevant for new hydrogen-generation technologies based on the same paradigm.

Embodiment 2: A $H_2$-PES System Based on PSII/PSI onto GO Thin Films

A photoelectrochemical system with a higher level of solid-state integration as shown schematically in FIG. 6 *a*) was assembled. The proposed system has the advantage of allowing the modular photosynthetic study of the individual components, unlike a $H_2$-generating GO suspension. FIG. 6 *b*) present the corresponding energy level diagram in terms of work functions, redox levels, energy gaps of GO, PSII/PSI, HOMO/LUMO energies of the electron transport layer (ETL). In FIG. 6 *a*) PSII and PSI CCs are immobilized onto GO deposited on ITO glass electrodes on the stroma and lumen side, respectively. These electrodes reside in separate compartments in electrical contact directly through GO or ITO or gold connection. The PSI side is connected in parallel to the PSII side. A direct transfer from PSII to GO is assumed, which can be accomplished alternatively using redox mediators. Electron transfer is easier through 8%-oxygen GO on the PSII side. PSI is interfaced with an aluminum tris(8-hydroxyquinoline) $Alq_3$ ETL deposited onto it by thermal evaporation as suggested in literature. 20%-oxygen content GO is used. Since this type of GO is a preferential hole-conductor, it effectively promotes charge separation across the PSI side of the device avoiding short-circuit. A Pt layer deposited on top of PSI by thermal evaporation is in electrical contact, therefore electrically equipotential with a gas diffusion electrode (GDE). The GDE is comprised of a Pt spongy electrode or by a layer of Pt particles embedded in supporting carbon. The protons produced by the oxidation of water by PSII are transported to the Pt-GDE by a proton conducting membrane comprised of an appropriately prepared Nafion® film. Water is the reactant in this device and it is gravity-fed into the PSII compartment. Alternatively, a simplified version of it is comprised of PSII CCs and PSI-CC-Pt (or PSI-CC-HG) directly attached to a GO thin film. The next section illustrates how to engineer a prototype system.

Photoelectrochemical Hydrogen Production Based on PSII/PSI Photosynthetic Core Complexes: $H_2$-PES Prototype Based on GO Thin Films Engineering In FIG. 7 *a*) a prototype for hydrogen generation is presented. This system is designed in order to achieve the solid state integration of PSII and PSI in a device. The main features of the system consist of a water tank, a hydrogen tank and a Teflon core hosting the PSII-GO-ITO and PSI-GO-ITO electrodes. As shown in FIG. 7 *b*) the Teflon core allows the rapid insertion of surface modified CC-GO-ITO glasses into lateral slots (slots A and B) and insures waterproof and gas proof seals. The water tank has a cap that is also a hydrophobic filter in order to selectively allow the release of oxygen gas and prevent water evaporation. The photosystem stoichiometry, namely the ratio PSII to PSI, can be changed by changing the area of PSI-GO-ITO with respect to that of PSII-GO-ITO or by controlling the protein loading of the photosystems on the surface.

It should be noticed that since water is the fuel in this system it is not possible to obtain an entirely solid device except by using an aqueous gel as the electrolyte in the PSII compartment. The Teflon core can also be modified in order to include light filters capable of ensuring appropriate low light irradiance to the photosynthetic centers.

Hydrogen Generation Efficiency of the Hydrogen-Generating Photoelectrochemical System ($H_2$-PES) Prototype Based on GO Thin Films The active area of the PSII-GO-ITO glass slide is $1.50 \times 3.00$ cm$^2$=4.50 cm$^2$, while the active area of the PSII-GO-ITO glass slide is $1.50 \times 6.00$ cm$^2$=9.00 cm$^2$. The inner volume of the water tank is $3.80 \times 3.30 \times 4.80$ cm$^3 \approx 60$ cm$^3$. The molar volume of water at room temperature is about 18 cm$^3$; therefore, the total number of moles of water in the water tank is 3.3 mol, in abundant excess with respect to the device requirements. The inner volume of the hydrogen tank is $3.50 \times 2.50 \times 22.0$ cm$^3$=193 cm$^3$. The pertinent semi-reactions are the following: $H_2O \rightarrow \frac{1}{2}O_2 + 2H^+ + 2e-$ and $2H^+ + 2e- \rightarrow H_2$ (Pt). In order to produce a working pressure of 2 atm in the hydrogen tank, $1.6 \cdot 10^{-2}$ mol of water needs to be hydrolysed to $1.6 \cdot 10^{-2}$ mol of hydrogen gas. In order to estimate how much time is required to generate such pressure the highest published photocurrent density that has been obtained from oriented PSII onto a gold surface is considered as a starting point. Such photocurrent was equal to 14 µA/cm$^2$ under low light conditions (100 µmol quanta·m$^{-2}$·s$^{-1}$). It can be assumed that this photocurrent represents the limiting step in the device since PSI-GO-ITO is expected to deliver higher photocurrent levels. Considering the active surface of the PSII-GO-ITO electrode it is calculated that a current of 63 µA is produced in the device. By dividing the total current produced by the Faraday constant (96,484 C/mol) the estimate the rate of hydrogen generation as equal to $3.3 \cdot 10^{-10}$ mol/s can be generated. By assuming 12 hours of light per day, it can be calculated that the device would require 1115 days to build up 2 atm of hydrogen pressure.

However, there are arguments in favour of the contrary.

1) The active area of the ITO-PSII glass slide in the device is very small (4.5 cm$^2$). Small area ITO glasses for easier surface modification can be used. Just by multiplying this area by a factor of 200 (which correspond to a ITO-PSII rectangle of only 42.4 cm by 21.2 cm) the same pressure could be built up in 5.6 days.

2) The possibility to increase the active surface could also be achieved by stacking active units. This approach would result in more compact design of subsequent versions of the $H_2$-PES prototype.

3) Multiple-layer structure electrodes are possible. Previous work has shown that current as high as 45 µA/cm$^2$ can be obtained at 100 mmol quanta·m$^{-2}$·s$^{-1}$.

Improving upon the proposed $H_2$-PES prototype based on GO thin films is achievable by producing $H_2$-generating GO suspensions.

Embodiment 3: A H$_2$-HPES based on PSII/PSI onto on GO-Polymer Composites

A H$_2$-generating photoelectrochemical system which allows the separation of the hydrogen evolving reaction from the oxygen evolving reaction is shown schematically in FIG. 8 a). It should be noticed that the GO flakes are vertically oriented on the proton/electron transport layers (PETLs). The high surface advantage provided by the GO single-layers is preserved in this hierarchical system, producing an enhanced planar junction geometry. FIG. 8 b) presents the corresponding energy level diagram in terms of work functions, redox levels, energy gaps of GO, PSII/PSI, the HOMO/LUMO energies of the PETL layers (polyaniline or PANI, or sulfonated PANI). In FIG. 8 a) PSII and PSI are immobilized onto GO single-layers on the stroma and lumen side, respectively, embedded in a PETL layer. The immobilization of PSII CCs or PSI-CC-Pt is carried out on a PETL spin-coated on a glass support; then the resulting membrane is peeled off the support. The two PETL layer bearing PSII and PSI-CC-Pt can be matched back-to-back in order to separate two compartments in electrical contact directly through GO and the PETL layers. Electron transfer is easier through 8%-oxygen GO. The PETL layers also ensure protonic contact. The evident benefit of this configuration is the possibility of substituting PSI-CC-HG for PSI-CC-Pt. This configuration can be easily engineered by immobilizing the PSII-GO-(PETL)$_2$-PSI-Pt or the PSII-GO-(PETL)$_2$-PSI-HG membrane within the hole of a Teflon support which separates two Teflon or glass compartments for the oxygen and hydrogen evolution reactions.

Hydrogen Generation Efficiency of H$_2$-HPES Systems Based on GO-Polymer Composites If the GO flakes were not vertically oriented but instead horizontally oriented giving an exposed thin film, a simple planar junction configuration device would be achieved. The pertinent semi-reaction are the following: H$_2$O→½O$_2$+2H$^+$+ 2e– and 2H$^+$+2e–→H$_2$ (Pt). In order to estimate the hydrogen generation efficiency, it is possible to consider as a starting point the highest-published photocurrent density that has been obtained from oriented PSII CCs onto a gold surface. Such photocurrent was equal to 14 µA/cm$^2$ under low-light conditions (100 mmol quanta·m$^{-2}$·s$^{-1}$). It can be assumed that this photocurrent corresponds to the best current that can be generated by a PSII-GO-PETL electrode. It can also be assumed that this photocurrent represents the limiting step in the device since PETL-GO-PSI-Pt is expected to deliver higher photocurrent levels. It can be estimated that the rate of hydrogen generation is equal to $3.7 \cdot 10^{-11}$ mol/(cm$^2$·s) in a 2:1 PSII:PSI stoichiometry (see below). It is clear that the vertical orientation of the GO flakes on the PETL layers provides substantial surface increment with respect to the planar configuration. The available surface of the GO flakes and their numerical density on the PETL layers will determine the size of this "surface advantage." In the following section, the efficiency of H$_2$-generating suspensions in which the GO flakes are unbounded is estimated, which represents the upper limit for the configuration based on PETLs.

Parameters Affecting the Quantum Yield of Biosolar Hydrogen Production by the Proposed H$_2$-HPES System based on GO Thin Films, H$_2$-HPES System based on GO-Polymer Composites, and for the Hybrid Photosynthetic GO Suspensions. The quantum efficiency of hydrogenase-dependent biosolar hydrogen production in terms of the incident solar spectrum, at wavelengths that are absorbed by, and result in, photochemical turnover of the photosynthesis, can be evaluated by using the following equation:

$$QY(H_2) = \Lambda_i(1-\Lambda_{NPQ})\Phi_1\Phi_2(1-X_c)(1-X_A)(1-X_N)(1-X_O)(1-\Omega_2) \quad (1)$$

(i) $\Lambda_i$ is the fraction of the incident solar light in the interval ~380 nm-740 nm that is absorbed and available for photosynthesis. $\Lambda_i$ is equal to 43%. (ii) $\Lambda_{NPQ}$ is the fraction of light in the antenna complexes that is lost due to non-photochemical quenching in order to prevent PSII oxidative damage due to excess light (30). This fraction is lost as heat and can be as high as 80% under high light conditions (high irradiance). (iii) $\Phi_1$ and $\Phi_2$ are the photochemical quantum yield of PSI and PSII, respectively. $\Phi_1$ is equal to 80±10%, while $\Phi_2$ is equal to about 45±10%[31]. The loss in PSII is due to charge recombination or fluorescence. (iv) X is the branching fraction of electron flux from ferredoxin into competing pathways: $X_C$ is for CO$_2$ fixation, $X_A$ for ATP generation, $X_O$ for oxygen reduction by PSI, and $X_N$ is for nitrogen fixation if a nitrogen source is available. (v) $\Omega_2$ is the fraction of PSII centers photoinactivated by Visibile and UV light. Photoinactivation can happen through at least two types of mechanisms: a) aberrant photochemistry associated with PSII lacking the CaMn$_4$ cluster; b) direct exposure of CaMn$_4$ cluster to UV light. Equation (1) is used to evaluate the photon conversion efficiencies of photosynthetic organisms.

It is possible to adapt equation (1) to estimate the hydrogen quantum yield of the proposed prototype, by considering only the relevant factors:

$$QY(H_2) = \Lambda_i \Phi_1 \Phi_2 \epsilon_e \quad (2)$$

The values of the first three factors were specified above. Non-photochemical quenching is not relevant because the CCs lack the appropriate proteins for this mechanism. Photoinactivation of PSII is not considered. It can be assumed that all the PSII centers have an active Mn$_4$Ca cluster. In the computation of the quantum yield, it is reasonable to include the electrochemical efficiency $\epsilon_e$. This factor is related to irreversible voltage losses. $\epsilon_e$=83% as working value can be assumed, in analogy with the average electrochemical efficiency of a polymer electrolyte fuel cell. Therefore a hydrogen quantum yield of 13% to 18% for the prototype is epxected. The theoretical hydrogen quantum yield of the hydrogen-generating system would be 15% to 21%. Considering the values for $\Phi_1$ and $\Phi_2$ of 100% and 85%, respectively, sometimes found in the literature, a hydrogen quantum yield of 30% and a theoretical hydrogen quantum yield of 37% would be obtained. Similar theoretical hydrogen quantum yields can be assumed also in the case of H$_2$-generating GO suspensions and of the H$_2$-HPES Prototype based on GO-Polymer Composites.

Bio-Mimetic and Hybrid Photoelectrochemical Devices

The discussion presented above implies that a hydrogen generation system based on semi-artificial photosynthesis is certainly feasible. A serious issue is represented by the limited lifetime of isolated PSII CCs. The turnover number of ~1,000,000 of the D$_1$ protein is hard to bypass unless repair mechanisms could be set in place. Alternatively, an open system in which PSII CCs are periodically removed is feasible.

The H$_2$-PES systems based on GO thin Films, GO suspensions and GO-polymer composites involving isolated photosynthetic complexes and Platinum provide special cases of a more general paradigm for construction of hydrogen generating systems based on CMG The schematic representation of this paradigm, in the case of a CMG suspension, is illustrated in FIG. 9. CMG is the platform for a photoanode and photocathode nanoparticles. In some cases, the distinction between photoanode and photocathode is not applicable as some semiconductors have a band-gap which straddles both water oxidation and proton reduction and therefore can split water as such. Also, in FIG. 9 left or right do not have a strict meaning when dealing with CMG suspensions. CMG platelets provide an equipotential surface where both the photoanodes and photocathodes are attached, sometimes on the same side of the CMG layer.

The photoanode nanoparticles can be comprised of, beside PSII CCs, by semiconductors with a band-gap straddling the oxygen evolving reaction (OER), by semiconductors coated with a catalyst for OER, or by metals capable of OER. OER catalysts can have an extended structure (also including the case of a molecular structure embedded in an extended structure) and a molecular molecular structure.

Semiconductors or semiconductors modified on the surface with fixed dipoles or charges that can be used as photoanode nanoparticles are the following: metal oxide or metal oxide anions (oxometallates) in pure, mixed or doped form; n-$Fe_2O_3$, n-$WO_3$, n-$TiO_2$, ZnO, $SrTiO_3$, $BaTiO_3$, $SrTiO_3$ with Rh or Pt, La-doped $NaTaO_3$ with NiO as a co-catalyst, $La_2Ti_2O_7$, $La_2Ti_2O_7$ with Ba, $K_2La_2Ti_3O_{10}$, $Ba_5Nb_4O_{15}$, $Sr_2Ta_2O_7$, $Ba_5Ta_4O_{15}$, $KTaO_3$, $Gd_2H_2O_7$, $Y_2Ti_2O_7$, $Cs_2Nb_4O_{11}$, Zn-doped $Ga_2O_3$, alkylated Si (e.g. methylated Si), F-doped $TiO_2$ or $Fe_2O_3$, Si-doped $Fe_2O_3$, metal oxides with early transition metals (e.g. Ce(IV), Ti(IV), Zr(IV), Nb(V), Ta(V)) and $d^{10}$ ions (e.g. Zn(II), Ga(III), Ga(IV), Sn(IV), Sb(V)), GaN, β-$Ge_3N_4$; $d^{10}$ and $d^{10}s^2$ oxides of $Cu^+$, $Ag^+$, $Cd^{2+}$, $Hg^{2+}$, $In^{3+}$, $Tl^{3+}$, $Sn^{2+}$, $Pb^{2+}$ and $Bi^{3+}$ (e.g. $In_2O_3$, α-PbO); $BiVO_4$, $PbMo_{1-x}Cr_xO_4$, $InVO_4$, $InNbO_4$, $InTaO_4$ with a NiO cocatalyst, $BiYWO_6$, $PbBi_2Nb_2O_9$, α-$Fe_2O_3$, $SnO_2$, mixed oxide semiconductors (e.g. $Ti_xFe_yO_z$, $TiO_2$ co-doped with $Cr^{3+}/Sb^{5+}$ or $Rh^{3+}/Sb^{5+}$), GaN:ZnO, $Rh_{2-x}Cr_xO_3$, (oxy)nitrides of Ti and Ta (e.g. TaON), CdS, GaP protected by Sn-doped $In_2O_3$ with $RuO_2$ as cocatalyst, $CdS_{1-x}Se_x$, n-GaAs covered with $MnO_2$, Extended solid-state OER catalysts in acid and/or alkaline media include but are not limited to: perovskite $M(OH)_3$ materials with M=Cr, Mn, Fe, Co, Ni; metal oxide surfaces such as $TiO_2$, nitrogen-doped $TiO_2$, $PbO_2$, $NiO_x$, $MnO_2$, $PtO_2$, $IrO_2$, $RuO_2$, $CoO_3$, $Fe_3O_4$; mixed metal oxides, in particular spinels with general formula $(M')_x(M'')_{3-x}O_4$, based on the binary synergism M'-M" such as Co—Ni, Ni—Cu, Co—Mo, Fe—Mo, Cu—Co, or ternary synergism Co—Cr—Fe; nanoparticles of $IrO_2$ and $Co_3O_4$ o Ti; self-healing, self-assembling Co-based (Co phosphate or Co—$P_i$) and Ni-based OER catalysts; $LaMnO_3$, $LaCoO_3$, $LaNO_3$, and $IrO_2$—$Ta_2O_5$, $MnO_2/MnO_3$, $SrFeO_3$, $La_{0.6}Sr_{0.4}CoO_3$, $NiLa_2O_4$, $NiCo_2O_4$, $LaCoO_3$, $Pb_2Ru(Ir)_2O_7$.

Molecular OER catalysts in acid and/or alkaline media include but are not limited to: $[(bpy)_2(H_2O)Ru^{III}(\mu\text{-}O)Ru^{III}(OH_2)(bpy)_2]^{4+}$ with bpy=2,2'-bipyridine; $[Ru^{III}(NH_3)_5Cl]^{2+}$ on Pt black; $[Ru^{III}(NH_3)_5Cl]^{2+}$; RuO on Ti; $[(NH_3)_5Ru^{III}(\mu\text{-}O)Ru^{III}(NH_3)_5]^{4+}[(NH_3)_5Ru(\mu\text{-}O)Ru(NH_3)_4(\mu\text{-}O)Ru(NH_3)_5]^{6+}$ on Pt black; $[(NH_3)_5Ru(\mu\text{-}O)Ru(NH_3)_4(\mu\text{-}O)Ru(NH_3)_5]^{6+}$; $[Ru(Mebimpy)(4,4'\text{-}((HO)_2\text{—}OPCH_2)_2bpy)(OH_2)]^{2+}$ with Mebimpy=2,6-bis(1-methyl benzimidazol-2-yl)-pyridine; $[(tpy\text{-}PO_3H_2)\text{—}(H_2O)_2Ru^{III}]_2O^{4+}$ with tpy=2,2':6,2"-terpyridine; $[Ru_2(\mu\text{-}bpp)(\mu\text{-}OAc)(t\text{-}trpy)_2]^{2+}$ with bpp=bis(2-pyridyl)pyrazolato, t-trpy=4'-(para-pyrrolylmethylphenyl)-2,2':6',2"-terpyridine; $[Ru_2(OH)(3,6\text{-}tBu_2qui)_2(btpyan)](SbF_6)_2$ with qui=quinone, btpyan=1,8-bis(2,2':6', 2"-terpyridyl)anthracene; $[Ru^{III}(tpy)\text{-}(bpm)(OH_2)]^{2+}$ and $[Ru^{III}(tpy)(bpz)(OH_2)]^{2+}$ with tpy=2,2':6,2"-terpyridine, bpm=2,2'-bipyrimidine, bpz=2,2'-bipyrazine); $Mn_4O_4$ cubanes such as $[Mn_4O_4((p\text{-}MeOPh)PO_2)_6]^+$; polyoxometallates such as $[Ru^{III}_2Zn_2(H_2O)_2(ZnWO_{34})_2]^{14-}$, $Ru_4(H_2O)_4(\mu\text{-}O)_4(\mu\text{-}OH)_2(\gamma\text{-}SiW_{10}O_{36})_2]^{10-}$, $[Co_4(H_2O)_2(PW_9O_{34})_2]^{10-}$; cyclometalated bis-phenylpyridine diaquo iridium(III) complexes, iridium(III) complexes ligated by pentamethylcyclopentadienyl (Cp*); and porphyrins and corroles in Pacman and Hangman motifs.

The photocathode nanoparticles can be comprised of, beside platinized PSI CCs or PSI CCs wired to Pt nanoparticles, by semiconductors with a band-gap straddling the hydrogen evolving reaction (HER), by semiconductors coated with a catalyst for HER, or by metals capable of HER. HER catalysts can have an extended structure (also including the case of a molecular structure embedded in an extended structure) and a molecular structure.

Semiconductors or semiconductors modified on the surface with fixed dipoles or charges that can be used as photocathode nanoparticles are the following: p-Si, p-InP, p-GaP, p-GaAs, p-CdTe, p-InP decorated with Pt, oxidized InP decorated with Ru, p-InP deocorated with Rh or Re, p-Si with Pt, methylated p-Si with Pt, n-Si with Ni, p-SiC with Pt, GaAs with porphyrins on the surface, $GaInP_2$ with quinolinol groups on the surface, p-$GaInP_2$ in acidic conditions, group IV selenides with methyl viologen as redox mediator, $MoSe_2$, $WSe_2$, p-$WS_2$, $CuIn_xGa_yS_2$, $CuGaSe_2$, $Cu_2O$.

Extended solid-state OER catalysts in acid and/or alkaline media include but are not limited to: Tl, In, Cd, Pb, Ga, Zn, Ag, Sn, Bi, Cu, Fe, Co, Ni, Au, Pt, Rh, Ir, Re, W, Mo, Ti, Nb, Ta; binary alloy or intermetallics (e.g. Ni—Ti, Ni—Fe, Mo—Ni, Mo—Co, Mo—Pt, Ni—Zr, Mo—S, Ni—Mo—Cd, Ni—Mo—Fe, $La_5Ni$); $RuO_2$—$IrO_2$, WC, heteropolyacids (e.g. $H_3PMo_{12}O_{40}$) activating metals (e.g. Ni, Co, Pd, Fe); dealloyed metals from binary alloys (Ni Raney from Ni—Al alloys) and dealloyed binary alloys from ternary alloys.

Molecular HER catalysts in acid and/or alkaline media include but are not limited to: $Ni^{2+}$ and $Co^{2+}$ tetraazamacrocycles (capable of both proton and $CO_2$ reduction); $Ni^{2+}$-cyclam; $Co^{2+}$ complexes of hexadentate azamacrocycles; Cobalt diglyoxime complexes including $Co^{III}(dmgH)2(Py)(Cl)$ (in acetonitrile with $Et_3NH(BF_4)$) and related $Co^{II}$ complexes of difluoroboryl-glyoxime macrocycles with or without tetra-imine ligand; Co tetra-imine complexes in acidic aqueous solution; $Co(dmgBF_2)(CH_3CN)_2$ in acetonitrile with $CF_3COOH$; $Co(PY_4)(CH_3CN)_2$ with PY4=2-bis(2-pyridyl)-(methoxy)methyl-6-pyridylpyridine in $CH_3CN$ containing $CF_3COOH$; Co and Pt porphyrins in $HClO_4$; Co-phthalocyanin in phosphate buffer; $[Ni(P_2^{Ph}N_2^{Ph})_2(CH_3CN)](BF_4)_2$ with $P_2^{Ph}N_2^{Ph}$=1,3,5,7-tetraphenyl-1,5-diaza-3,7-diphospha-cyclooctane in $CH_3CN$ containing $CF_3SO_3H$ or acid water or $CH_3CN$ contaiing acid DMF; $CpMo(\mu\text{-}S)_2S_2CH_2$ in $CH_3CN$ containing p-cyanoanilinium; $[(PY_5Me_2)MoO](PF_6)_2$ with $PY_5Me_2$=2,6-bis(1,1-bis(2-pyridyl)ahyl)pyridine in phosphate buffer; [Fe]—, [FeFe]—, and [FeNi]-hydrogenases and complexes modeled after their active sites; $[\mu\text{-}S\text{-}2\text{-}(4\text{-}FC_6H_4CONHC_6H_4)]_2[Fe_2(CO)_6]$ or $[(\mu\text{-}1,2\text{-}benzenedithiolato)][Fe_2(CO)_6]$ in acetonitrile with $CH_3COOH$; dithiolatobridged $[(CO)_3Fe(pdt)(\mu\text{-}H)Ni(dppe)](BF_4)$ with pdt=propanedithiolate and dppe=1,2-bis(diphenylphosphino)ethane) in acetonitrile with $CF_3COOH$.

Binary systems with one photoanode and one photocathode can be extended to ternary or quaternary combinations of semiconductors or semiconductors coated with a catalyst. The inclusion of more than two semiconductor provide the benefit of a more efficient photon capture across the solar spectrum.

The medium for the suspension is an aqueous medium with or without additive for increasing its viscosity, such as PEO or detergents.

Hybrid systems involving the use of molecular biological components (e.g. PSI CCs, HGs) in conjunction with inorganic or metallorganic photoanode or photocathodes are possible.

Beside the suspension configuration, the thin-film and GO-polymer composite configurations are also possible.

Generation of Other Types of Fuels Supported by Chemically Modified Graphene $CO_2$ and $H_2O$ can in principle be converted into alkanes by metal-containing catalysts in two steps: 1) conversion to syngas (CO and $H_2$), 2) Fischer-Tropsch chemistry $nCO + 2nH_2 \rightarrow C_nH_{2n} + nH_2O$ and $nCO + (2n+1)H_2 \rightarrow C_nH_{2n+2} + nH_2O$ Immobilization of suitable catalysts onto CMG can provide the supporting carrier for these trasnsformations. For instance, reduction of $CO_2$ results in ethylene on Cu. Reduction of $CO_2$ results in formic acid on Hg, Pb, Sn, and Cd, while CO is obtained on Ag, Au, Zn, and Pd. Dimethyl ether and other oxygenates can be obtained by Fischer-Tropsch type (FT) catalysts involving Fe, Co, and Ni. $CO_2$ can be reduced to methanol on p-GaP electrode under illumination at 200-300 mV of underpotential in the presence of dissolved pyridinium (pyH+). The overpotential can be provided by a semiconductor (e.g. $n-Fe_2O_3$, $n-WO_3$, $n-TiO_2$)

Embodiment 4: Example of Hydrogen-Generation Using Semiconductors and Metal Catalysts onto Chemically Modified Graphene GO can be functionalized with oxidized InP decorated with Ru catalyst island using the native carboxylic group on the surface of GO or carboxylic groups generated on the surface of GO by standard methods. This system is capable of generating $H_2$ gas with an efficiency of 12%. Alternatively, p-InP deocorated with Pt, Rh or Re linked to GO by similar methods, will produce hydrogen with efficiencies of 13.3%, 13.3% and 11.4%, respectively.

Embodiment 5: A Cell-Free Cellulosome Based on Chemically Modified Graphene

Cellulosome are complexes of cellulotyc enzymes capable of digestion or degradation of biomass, plant cell materials, in particular cellulose. Glucose is typically the main product. GO can be utilized to immobilize cellulosome on its surface to facilitate cellulose degradation. One scheme consists in including His-tagged SdbA, a membrane-bound protein anchoring cellulosome to external bacterial surfaces. Therefore, cellulosome can be bound to the surface of GO through SdbA. SdbA is attached to the surface of GO by Ni-NTA functional groups. Each SdbA molecule contains one type II cohesin which is capable of interacting with one type II dockerin. Cellulosome complexes containing nine type I cohesin molecules (CipA), one cellulose-specific family 3 carbohydrate-binding module (CBM3A) and one type II dockerin can bind to single His-tagged SdbA anchored to the surface of GO through type II cohesin-dockerin interactions. This approach simplifies the number of proteins that need to be His-tagged, since only SdbA needs to be tagged. Individual enzymes and proteins can be obtained directly from unmodified cells still assembled in a cellulosome or isolated from recombinant sources and reassembled subsequently. Up to nine cellulose-degrading enzymes can be immobilized through type I cohesins. An alternative approach includes His-tagged CipA molecules attached directly to GO alongside a smaller proportion of His-tagged CBM molecules. Cellulose-degrading enzymes are bound to CipA molecules, while CBM is utilized to target GO to cellulose anchoring the enzyme assembly near the site of enzymatic activity. These approaches reflect many architectures observed in bacterial cellulosomes and could be open to modular optimization of enzymes towards specific sources of cellulose materials. These two approaches do not exhaust the possibilities for binding cellulosomes to GO. Cellulosomes are complex assemblies and as such can be anchored in different positions using alternative linking strategies, based on covalent, coordinative, ionic, hydrophobic/hydrophilic interaction chemistry.

Embodiment 6: Cell-Free Ethanol Production Based on Chemically Modified Graphene CMG can be used as a platform for the conversion of glucose into ethanol. Glucose is derived from natural resources such as corn, wheat, cellulosic biomass etc. A cocktail of 12 enzymes isolated from natural resources (e.g. yeast) is required (see FIG. 10). Each of these enzymes can be immobilized by covalent methods onto GO using exposed amino acid residues on the enzymes. These enzymes are 1) hexokinase (HK), which catalyze the transformation of glucose (Glc) to glucose-6-phosphate (G6P) in the presence of ATP; 2) phosphoglucoisomerase (PGI) which turn G6P into fructose-6-phosphate (F6P); 3) phosphofructokinase (PFK) turns F6P into fructose-1,6-bisphosphate (F16BP) in the presence of ATP; 4) aldolase (Ald) turns F16BP into dihydroxyacetone phosphate (DHAP) or glyceraldehyde-3-phosphate (GAP); 5) DHAP is in equilibrium with GAP via the intervention of triose-phosphate isomerase (TPI); 6) GAP is turned into 1,3-bisphosphoglycerate (BPG) by glyceraldehyde-3-phosphate dehydrogenase (GAPDH) in the presence of phosphate ($P_i$) and $NAD^+$; 7) BPG is turned into 3-phosphoglycerate (3PG) by phosphoglycerate kinase (PGK) in the presence of ATP; 8) 3PG is turned into 2-phosphoglycerate (2PG) by phosphoglycerate mutase (PGM); 9) 2PG is turned into phosphoenolpyruvate (PEP) by enolase (Eno); 10) PEP is turned into pyruvate (Pyr) by pyruvate kinase (PK) in the presence of ATP; 11) Pyr is turned quantitatively into acetaldehyde (AcAl) by pyruvate decarboxylase (PDC); 12) AcAl is turned into ethanol (EtOH) by alcohol dehydrogenase (ADH) in the presence of NADH; 13) ATP synthase (ATPase) prevents excess accumulation of ATP turning it into ADP.

Enzyme concentration levels can be manipulated at will.

The resulting system is viable at higher concentration of ethanol and higher temperature. The use of aresenate instead of phosphate by GAPDH results in the synthesis of 1-arseno-3-phosphoglycerate, which rapidly breaks down to arsenate and 3-phosphoglycerate (3PG). This step bypasses the need for ATP in the PGK step. Another strategy for solving the ATP accumulation problem is the engineering of PFK removing the allosteric site capable of binding ATP.

In summary, the resulting catalytic system for ethanol generation can generate ethanol at a rate greater than 3.7 mM per mM, on the basis of a total enzyme loading greater than 2.7 mg/mL. This rate of ethanol production is at least two times the maximum rate calculated on the basis of the physiological enzyme level.

Other embodiments are within the scope of the claims.

What is claimed is:

1. A material, comprising:
   a graphene derivative comprising a graphene core and a first pendant group, the first pendant group comprising a metal ion and a linking group wherein the metal ion is complexed with the linking group and the linking group is covalenty bonded to the graphene core.

2. The material of claim 1, wherein the linking group comprises a nitrilotriacetic acid moiety, a tris-nitrilotriacetic acid moiety, or an iminodiacetic acid moiety.

3. The material of claim 1, wherein the linking group is covalently bonded to the graphene core through an amide group.

4. The material of claim 1, wherein the first pendant group further comprises a His-tagged protein binding to the metal ion.

5. The material of claim 4, wherein the His-tagged protein is His-tagged Protein A or His-tagged Protein G.

6. The material of claim 1, wherein the metal ion is $Ni^{2+}$, $Cu^{2+}$, $Zn^{2+}$, $Ag^+$, $Fe^{3+}$, $Ga^{3+}$, $Zr^{3+}$, $Ca^{2+}$, or $Co^{2+}$.

7. A material, comprising:
a graphene derivative comprising a graphene core and a first pendant group, the first pendant group comprising a $SiO_2$ nanoparticle covalently bonded to the graphene core through an amide group.

8. The material of claim 7, wherein the $SiO_2$ nanoparticle is covalently bonded to the graphene core through a linkage —CO—NH—R—Si(—O—)$_3$, in which R is $C_1$-$C_{20}$ alkylene.

9. The material of claim 7, wherein the graphene derivative further comprises a second pendant group, the second pendant group comprising metal ion or a $TiO_2$ nanoparticle.

10. A chromatography column, comprising a column made from metal, glass, or plastic packed with a material comprising a graphene derivative comprising a graphene core and a first pendant group, the first pendant group comprising a metal ion, a nanoparticle, a sulfonate group, an amine group, a quaternary ammonium group, or a chelating group wherein the first pendant group is attached to the graphene core covalenty, or complexed ionically or coordinatively to one or more linking group covalently bonded to the graphene core.

11. The column of claim 10, wherein the column further comprises a spacer mixed with the material.

12. The column of claim 11, wherein the spacer is an oxide or a polymer.

13. A chromatographic system, comprising the chromatography column of claim 10.

14. A method of isolating a protein from a sample, comprising:
disposing the sample in a dispersion comprising a material comprising a graphene derivative comprising a graphene core and a first pendant group, the first pendant group comprising a metal ion, a nanoparticle, a sulfonate group, an amine group, a quaternary ammonium group, a chelating group, or a protein wherein the first pendant group is attached to the graphene core covalenty, or complexed ionically or coordinatively to one or more linking group covalently bonded to the graphene core, thereby binding the protein to be isolated to the material to form a protein-bound material;
isolating the protein-bound material; and
recovering the protein from the protein-bound material.

15. The method of claim 14, wherein isolating the protein-bound material is carried out by centrifugation, filtration, or decantation.

16. The method of claim 14, wherein the first pendant group comprises a metal ion.

17. The method of claim 16, wherein the protein is a His-tagged protein, a FLAG-tagged protein, a HA-tagged protein, a myc-tagged protein, a GST-tagged protein, a MBP-tagged protein, or a lectin.

18. The method of claim 17, wherein the His-tagged protein is a His-tagged photosystem I core complex, a His-tagged photosystem II core complex, or a His-tagged bacterial reaction center.

19. The method of claim 14, wherein the first pendant group comprises a $TiO_2$ nanoparticle.

20. The method of claim 19, wherein the protein is a phosphoprotein.

21. The method of claim 20, wherein the phosphoprotein is an Fe receptor, a Ulk antibody, a calcineurin, a K chromatin immunoprecipitate, or a urocotin.

22. The method of claim 14, wherein the first pendant group comprises a protein.

23. The method of claim 22, wherein the protein in the first pendant group comprises Protein A, Protein G, or an E72G3 protein.

24. The method of claim 23, wherein the protein in the sample is an antibody having an Fe region.

* * * * *